(12) United States Patent
Rajan et al.

(10) Patent No.: US 10,040,806 B2
(45) Date of Patent: Aug. 7, 2018

(54) MICROBIOCIDALLY ACTIVE BENZOXABOROLES

(71) Applicant: Syngenta Participations AG, Basel (CH)

(72) Inventors: Ramya Rajan, Goa (IN); Daniel Stierli, Stein (CH); Renaud Beaudegnies, Stein (CH)

(73) Assignee: SYNGENTA PARTICIPATIONS AG, Basel (CH)

( * ) Notice: Subject to any disclaimer, the term of this patent is extended or adjusted under 35 U.S.C. 154(b) by 0 days.

(21) Appl. No.: 15/117,251

(22) PCT Filed: Feb. 13, 2015

(86) PCT No.: PCT/EP2015/053149
§ 371 (c)(1),
(2) Date: Aug. 8, 2016

(87) PCT Pub. No.: WO2015/121442
PCT Pub. Date: Aug. 20, 2015

(65) Prior Publication Data
US 2016/0347773 A1    Dec. 1, 2016

(30) Foreign Application Priority Data
Feb. 17, 2014    (IN) .............................. 448/DEL/2014

(51) Int. Cl.
*C07F 5/02*    (2006.01)
*A01N 55/08*    (2006.01)

(52) U.S. Cl.
CPC .............. *C07F 5/025* (2013.01); *A01N 55/08* (2013.01)

(58) Field of Classification Search
CPC .................................. C07F 5/02; A01N 55/08
USPC ............................................ 504/193; 568/6
See application file for complete search history.

(56) References Cited

U.S. PATENT DOCUMENTS

2007/0286822 A1* 12/2007 Sanders .................... A61K 8/49
424/49

FOREIGN PATENT DOCUMENTS

| WO | 2006/089067 A2 | 8/2006 |
|---|---|---|
| WO | 2007/078340 A2 | 7/2007 |
| WO | 2008/157726 A1 | 12/2008 |
| WO | WO-2008157726 | * 12/2008 |
| WO | 2009/140309 A2 | 11/2009 |
| WO | 2010/028005 A1 | 3/2010 |
| WO | 2011/037731 A1 | 3/2011 |
| WO | 2011/049971 A1 | 4/2011 |
| WO | 2013/050591 A2 | 4/2013 |

OTHER PUBLICATIONS

STN entry for Registry No. 943311-49-7 published 2007.*
Hernandez, V. et al.: "Discovery of Novel Class of Boron-based Antibacterials with Activity against Gram-Negative Bacteria", Antimicrobial agents and Chemotherapy, vol. 57, 2013, pp. 1394-1403.
International Search Report and Written Opinion for International Patent Application No. PCT/EP2015/053149 dated Apr. 8, 2015.

* cited by examiner

Primary Examiner — Jeffrey S Lundgren
Assistant Examiner — Michael J Schmitt

(57) ABSTRACT

Compounds of formula (I) are as defined in the claims, and their use in compositions and methods for the control and/or prevention of microbial infection, particularly fungal infection, in plants and to processes for the preparation of these compounds.

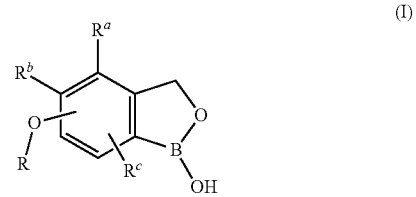

8 Claims, No Drawings

MICROBIOCIDALLY ACTIVE BENZOXABOROLES

RELATED APPLICATION INFORMATION

This application is a 371 of International Application No. PCT/EP2015/053149, filed 13 Feb. 2015, which claims priority to Indian Patent Application No. 448/DEL/2014, filed 17 Feb. 2014, the contents of which are incorporated herein by reference.

The present invention relates to novel microbiocidally active, in particular fungicidally active, oxoborazoles moiety containing compounds their use in compositions and methods for the control and/or prevention of microbial infection, particularly fungal infection, in plants or plant propagation material, harvested food crops by phytopathogenic microorganisms, preferably fungi and to processes for the preparation of these compounds. Preferably these compounds are used in agriculture or horticulture for controlling or preventing infestation of plants by phytopathogenic microorganisms, preferably fungi.

The incidence of serious microbial infections, particularly fungal infections, either systemic or topical, continues to increase for plants.

Fungicides are compounds, of natural or synthetic origin, which act to protect plants against damage caused by fungi. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations continues to be a major problem. Furthermore, fungicide resistance has become a serious problem, rendering these agents ineffective for some agricultural uses. As such, a need exists for the development of new fungicidal compounds with improved antifungal properties. It has been found that novel oxoborazoles with a specific substitution pattern are novel and have improved microbiocidal activity.

The present invention therefore provides a compound of formula (I)

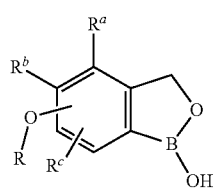

wherein
$R^a$ and $R^b$ and $R^c$ independently are H, fluorine, chlorine, bromine, cyano, nitro, unsubstituted or substituted $C_1$-$C_6$alkyl or unsubstituted or substituted $C_1$-$C_6$haloalkyl, unsubstituted or substituted $C_1$-$C_6$alkoxy, unsubstituted or substituted $C_1$-$C_6$haloalkoxy, unsubstituted or substituted $C_2$-$C_6$alkenyl, unsubstituted or substituted $C_2$-$C_6$alkynyl;
R is H, unsubstituted or substituted $C_1$-$C_6$alkyl, unsubstituted or substituted $C_1$-$C_6$haloalkyl, unsubstituted or substituted with five to ten ring membered aryl-A-, unsubstituted or substituted heteroaryl with 5 to 7 ring members comprising heteroatoms selected form O, S and N, unsubstituted or substituted $C_3$-$C_6$cycloalkyl or substituted $C_3$-$C_6$heterocyloalkyl ring members comprising heteroatoms selected form O, S and N, $C_2$-$C_6$alkenyl, $C_2$-$C_6$alkynyl, C(O)R', C(O)OR', S(O)$_n$R'
R' is H, unsubstituted or substituted $C_1$-$C_6$alkyl, unsubstituted or substituted $C_1$-$C_6$haloalkyl, unsubstituted or substituted aryl, unsubstituted or substituted heteroaryl
n is an integer 0 to 2;
A is a bridging element selected from —$C_{1-4}$alkylene, —C(O)—, $C_{1-4}$alkylene-C(O)—, —C(O)—$C_{1-4}$alkylene wherein the alkylene bridges may be unsubstituted or substituted like an alkyl group;
or
if the moiety O—R is in the position 6 and the substituent $R^c$ is in the position 7R forms a 5 to 7 membered ring with either $R^b$ or $R^c$ and this 5 to 7 membered ring may contain further heteroatoms selected form O, S and N; or
if the moiety O—R is in the position 7 and the substituent $R^c$ is in the position 6R forms a 5 to 7 membered ring with $R^c$ and this 5 to 7 membered ring may contain further heteroatoms selected form O, S and N;
and if R is methyl at least one of the $R^a$ and $R^b$ and $R^c$ is not H;
and agronomically acceptable salts, stereoisomers, diastereoisomers, enantiomers, tautomers, atriopisomers and N-oxides of those compounds.

The present invention accordingly further relates to a method for controlling or preventing for infestation of plants or plant propagation material and/or harvested food crops susceptible to microbial attack by treating plants or plant propagation material and/or harvested food crops with an effective amount of benzoxaborole derivatives according to formula (I) including the compound of formula (I) where R is methyl all of the $R^a$ and $R^b$ and $R^c$ are H and salts thereof.

The present invention accordingly further relates to the use of benzoxaborole derivatives according to formula (I) including the compound of formula (I) where R is methyl all of the $R^a$ and $R^b$ and $R^c$ are H and salts thereof for controlling or preventing infestation of plants or plant propagation material, the application of benzoxaborole derivatives according to formula (I) including the compound of formula (I) where R is methyl all of the $R^a$ and $R^b$ and $R^c$ are H to useful plants, the application of benzoxaborole derivatives according to formula (I) including the compound of formula (I) where R is methyl all of the $R^a$ and $R^b$ and $R^c$ are H to the locus of useful plants or the application of benzoxaborole derivatives according to formula (I) including the compound of formula (I) where R is methyl all of the $R^a$ and $R^b$ and $R^c$ are H to plant propagation material of useful plants a compound of formula (I) including the compound of formula (I) where R is methyl all of the $R^a$ and $R^b$ and $R^c$ are H.

The present invention accordingly further relates to the use of benzoxaborole derivatives according to formula (I) including the compound of formula (I) where R is methyl all of the $R^a$ and $R^b$ and $R^c$ are H and salts thereof for controlling or preventing infestation of plants or plant propagation material by treating plants or plant propagation material with an effective amount of an benzoxaborole of general formula (I) including the compound of formula (I) where R is methyl all of the $R^a$ and $R^b$ and $R^c$ are H.

The present invention accordingly further relates to the method of controlling phytopathogenic diseases on useful plants or plant propagation material thereof, which comprises applying to said plant or plant propagation material a fungicidally effective amount of a compound of formula (I) including the compound of formula (I) where R is methyl all of the $R^a$ and $R^b$ and $R^c$ are H. Preferably the method of controlling phytopathogenic diseases on useful plants or plant propagation material thereof, which comprises applying to said plant or plant propagation material a fungicidally effective amount of a compound of formula (I) including the compound of formula (I) where R is methyl all of the $R^a$ and $R^b$ and $R^c$ are H, wherein plant propagation material of useful plants are seeds of useful plants.

The present invention accordingly further relates to the method for controlling or preventing infestation of plants or plant propagation material by treating plants or plant propagation material with an effective amount of an oxaborole of general formula (I) including the compound of formula (I) where R is methyl all of the $R^a$ and $R^b$ and $R^c$ are H.

The present invention accordingly further relates to the method of controlling phytopathogenic diseases on useful plants or plant propagation material thereof, which comprises applying to said plant propagation material a fungicidally effective amount of a compound of formula (I) including the compound of formula (I) where R is methyl all of the $R^a$ and $R^b$ and $R^c$ are H.

Accordingly the present invention also relates to a method of protecting plant propagation material and organs that grow at a later point in time against damage phytopathogenic diseases, which method comprises applying to said propagation material a fungicidally effective amount of a compound of formula I.

In a further aspect of the invention, the invention provides a plant propagation material protecting composition comprising a compound of formula I, together with a suitable carrier therefore.

In a further aspect of the invention, the invention provides a method of controlling phytopathogenic diseases on useful plants or plant propagation material thereof, which comprises applying to said plant propagation material a fungicidally effective amount of a plant propagation material protecting composition comprising a compound of formula (I) including the compound of formula (I) where R is methyl all of the $R^a$ and $R^b$ and $R^c$ are H as defined in claim 1, together with a suitable carrier therefore.

A preferred embodiment of this aspect of the invention is a plant propagation material protecting composition comprising a compound of formula I, together with a suitable carrier therefor, wherein said plant propagation material protecting composition comprises additionally a colouring agent.

In yet a further aspect of the invention, the invention provides plant propagation material treated with a plant propagation material protecting composition comprising a compound of formula I, together with a suitable carrier therefor.

A preferred embodiment of this aspect of the invention is plant propagation material treated with a plant propagation material protecting composition comprising a compound of formula I, together with a suitable carrier therefor, wherein said plant propagation material protecting composition comprises additionally a colouring agent.

A method of controlling or preventing pest damage in a growing plant said method comprising applying onto the plant propagation material, before planting or sowing thereof a compound of formula (I) including the compound of formula (I) where R is methyl all of the $R^a$ and $R^b$ and $R^c$ are H.

A method of controlling or preventing damage by phytopathogenic diseases in a growing plant or growing plant tissue said method comprising: applying onto the plant propagation material, before planting or sowing thereof a fungicidial effective amount of a compound of formula (I) including the compound of formula (I) where R is methyl all of the $R^a$ and $R^b$ and $R^c$ are H.

A method of controlling or preventing fungal diseases in a growing plant or growing plant tissue said method comprising: applying onto the plant propagation material before planting or sowing thereof a fungicidial effective amount of a compound of formula (I) including the compound of formula (I) where R is methyl all of the $R^a$ and $R^b$ and $R^c$ are H.

In a preferred embodiment the plant propagation material is a seed or a tuber. In a further preferred embodiment the plant propagation material is a seed. In a further preferred embodiment the plant propagation material is a tuber. Preferably the seeds and tubers (stem tubers and root tubers) according to this application are alive. Preferably the seeds and tubers according to this application are able to germinate.

In a further aspect of the invention, the invention provides a method of controlling or preventing damage by phytopathogenic diseases in a growing plant said method comprising applying onto the seed, before planting or sowing thereof a compound of formula (I) including the compound of formula (I) where R is methyl all of the $R^a$ and $R^b$ and $R^c$ are H.

In a further aspect of the invention, the invention provides a method of controlling or preventing damage by phytopathogenic diseases in a growing plant or growing plant tissue said method comprising: applying onto the seed, before planting or sowing thereof a fungicidial effective amount of a compound of formula (I) including the compound of formula (I) where R is methyl all of the $R^a$ and $R^b$ and $R^c$ are H.

In a further aspect of the invention, the invention provides a method of controlling or preventing fungal diseases in a growing plant or growing plant tissue said method comprising: applying onto the seed before planting or sowing thereof a fungicidial effective amount of a compound of formula (I) including the compound of formula (I) where R is methyl all of the $R^a$ and $R^b$ and $R^c$ are H.

In a further aspect of the invention, the invention provides a method of protecting plant propagation material and organs that grow at a later point in time against damage by phytopathogenic diseases, which method comprises applying to said propagation material a fungicidially effective amount of a compound of formula (I) including the compound of formula (I) where R is methyl all of the $R^a$ and $R^b$ and $R^c$ are H.

In a further aspect of the invention, the invention provides a plant propagation material comprising compound a compound of formula (I) including the compound of formula (I) where R is methyl all of the $R^a$ and $R^b$ and $R^c$ are H. Preferably the plant propargation material comprising a fungicidial effective amount of a compound of formula (I) including the compound of formula (I) where R is methyl all of the $R^a$ and $R^b$ and $R^c$ are H.

In a further aspect of the invention, the invention provides a plant propagation material comprising compound a compound of formula (I) including the compound of formula (I) where R is methyl all of the $R^a$ and $R^b$ and $R^c$ are H and comprises additionally a colouring agent.

In a further aspect of the invention, the invention provides a coated plant propagation material coated with a compound of formula (I) including the compound of formula (I) where R is methyl all of the $R^a$ and $R^b$ and $R^c$ are H.

In a further aspect of the invention, the invention provides a combination of a plant propagation material and a compound of formula (I) including the compound of formula (I) where R is methyl all of the $R^a$ and $R^b$ and $R^c$ are H.

In a further aspect of the invention, the invention provides a coated plant propagation material coated with coating comprising a compound of formula (I) including the compound of formula (I) where R is methyl all of the $R^a$ and $R^b$ and $R^c$ are H as defined in claim 1.

In a further aspect of the invention, the invention provides a plant propagation material comprising an outer coating characterized that the outer coating comprises a compound according to formula (I) including the compound of formula (I) where R is methyl all of the $R^a$ and $R^b$ and $R^c$ are H, preferably a seed comprising an outer coating characterized that the outer coating comprises a compound according to formula (I) including the compound of formula (I) where R is methyl all of the $R^a$ and $R^b$ and $R^c$ are H.

In a further aspect of the invention, the invention provides a composition comprising a plant propagation material and a compound of formula (I) including the compound of formula (I) where R is methyl all of the $R^a$ and $R^b$ and $R^c$ are H.

In a further aspect of the invention, the invention provides a composition comprising a plant propagation material and a compound of formula and further comprising a seed grow medium.

In a further aspect of the invention, the invention provides a plant which results from the germination of a a coated seed wherein the coating comprises a compound of formula (I) including the compound of formula (I) where R is methyl all of the $R^a$ and $R^b$ and $R^c$ are H.

In a further aspect of the invention, the invention provides a coated plant propagation material wherein the coating comprises a compound of formula (I) including the compound of formula (I) where R is methyl all of the $R^a$ and $R^b$ and $R^c$ are H.

In a further aspect of the invention, the invention provides a coated plant propagation material according to the preceding paragraph, wherein the said material is a seed.

In a further aspect of the invention, the invention provides the combination of a plant propagation material and a composition comprising a compound of formula (I) including the compound of formula (I) where R is methyl all of the $R^a$ and $R^b$ and $R^c$ are H.

In a further aspect of the invention, the invention provides the combination according to the preceding paragraph wherein the said material is a seed.

In a further aspect of the invention, the invention provides the combination according to one of the two preceding paragraphs, further comprising a plant growth and/or seed germination medium.

In a further aspect of the invention, the invention provides a plant which results from the germination and/or growth of the coated plant propagation material wherein the coating comprises a compound of formula (I) including the compound of formula (I) where R is methyl all of the $R^a$ and $R^b$ and $R^c$ are H.

In a further aspect of the invention, the invention provides a plant which results from the germination and/or growth of the coated plant propagation material wherein the coating comprises a compound of formula (I) including the compound of formula (I) where R is methyl all of the $R^a$ and $R^b$ and $R^c$ are H and wherein the coated plant propagation material is a seed. Preferably the coated plant propagation material is a seed.

In a further aspect of the invention, the invention relates to the use of a compound of formula (I) including the compound of formula (I) where R is methyl all of the $R^a$ and $R^b$ and $R^c$ are H according to claim 1, in the preparation of a composition for coating a plant propagation material for the prevention or control of plant pathogenic fungi.

In a further aspect of the invention, the invention relates to a method of controlling or preventing infestation of plants or plant propagation material and/or harvested food crops susceptible to microbial attack by treating plants or plant propagation material and/or harvested food crops with an effective amount of an oxaborole of general formula (I) including the compound of formula (I) where R is methyl all of the $R^a$ and $R^b$ and $R^c$ are H In a further aspect of the invention, the invention relates to a method of controlling or preventing infestation of plants or plant propagation material and/or harvested food crops susceptible to microbial attack by providing in a first step a agrochemical compositions according to the present invention comprising from 0.1 to 99% by weight of the compound of formula (I) including the compound of formula (I) where R is methyl all of the $R^a$ and $R^b$ and $R^c$ are H and 99.9 to 1% by weight, of a solid or liquid adjuvant and/or an surfactant and in a second step applying said composition to the plants or the locus thereof.

The compounds of formula I are applied by treating plant propagation material with a fungicidally effective amount of a compound of formula I. Preferably, compounds of formula I are applied by adhering compounds of formula I to plant propagation material in a fungicidally effective amount.

A preferred application method is seed treatment.

The method according to the invention is especially suitable to increase the yield and/or quality of useful plants, such as crop yield of crop plants.

The invention covers all agronomically acceptable salts, isomers, stereoisomers, diastereoisomers, enantiomers, tautomers, atropisomers and N-oxides of those compounds. The compounds of formula (I) including the compound of formula (I) where R is methyl all of the $R^a$ and $R^b$ and $R^c$ are H may exist in different geometric or optical isomeric forms or in different tautomeric forms. One or more centres of chirality may be present, in which case compounds of the formula (I) including the compound of formula (I) where R is methyl all of the $R^a$ and $R^b$ and $R^c$ are H may be present as pure enantiomers, mixtures of enantiomers, pure diastereomers or mixtures of diastereomers. There may be double bonds present in the molecule, such as C=C or C=N bonds, in which case compounds of formula (I) including the compound of formula (I) where R is methyl all of the $R^a$ and $R^b$ and $R^c$ are H may exist as single isomers or mixtures of isomers. Centres of tautomerisation may be present. This invention covers all such isomers and tautomers and mixtures thereof in all proportions as well as isotopic forms such as deuterated compounds. Also atropisomerism may occur as a result of a restricted rotation about a single bond.

Suitable salts of the compounds of formula (I) including the compound of formula (I) where R is methyl all of the $R^a$ and $R^b$ and $R^c$ are H include acid addition salts such as those with an inorganic acid such as hydrochloric, hydrobromic, sulphuric, nitric or phosphoric acid, or an organic carboxylic acid such as oxalic, tartaric, lactic, butyric, toluic, hexanoic or phthalic acid, or a sulphonic acid such as methane, benzene or toluene sulphonic acid. Other examples of organic carboxylic acids include haloacids such as trifluoroacetic acid.

N-oxides are oxidised forms of tertiary amines or oxidised forms of nitrogen containing heteroaromatic compounds. They are described in many books for example in "Heterocyclic N-oxides" by Angelo Albini and Silvio Pietra, CRC Press, Boca Raton, Fla., 1991.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine. Examples of bicyclic groups are benzothiophenyl, benzimidazolyl, benzothiadiazolyl, quinolinyl, cinnolinyl and quinoxalinyl.

The term "heterocyclyl" is defined to include heteroaryl and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The alkyl groups, the alkenyl groups, the alkynyl groups and the alkoxy groups in the compound of formula (I) are either linear or branched or they are perhalogenated and forming haloalkyl groups, haloalkenyl groups, haloalkynyl groups or haloalkoxy groups. Halogen signifies preferably F, Cl, Br, I, and more preferred halogen signify F or Cl. A oxo substituent is =O, thus a oxygen atom doubly bonded to carbon or another element. The term "oxo substituent" thus embraces aldehydes, carboxylic acids, ketones, sulfonic acids, amides and esters.

The preferred substituents of the substituted alkyl groups, the substituted alkenyl groups, the substituted alkynyl groups, the substituted alkoxy groups, substituted aryl groups and/or the aromatic heterocycle groups in the compound of formula (I) are selected from the following substituents F, Cl, Br, I, —OH, —CN, nitro, an oxo substituent, —$C_{1-4}$alkoxy, —$C_{1-4}$alkylthio, $C_{1-4}$alkyl, $C_{2-4}$alkenyl, $C_{2-4}$alkenyl, $C_{2-4}$alkynyl, —C(O)H, —C(O)($C_{1-4}$ alkyl), —C(O)($C_{1-4}$alkoxy), —C(O)NH$_2$, —C(O)NH($C_{1-4}$ alkyl), —C(O)N($C_{1-4}$ alkyl)($C_{1-4}$ alkyl), —OC(O)NH($C_{1-4}$ alkyl), —OC(O)N($C_{1-4}$ alkyl)($C_{1-4}$ alkyl), —NHC(O)($C_{1-4}$ alkyl), —NHC(O)($C_{1-4}$ alkoxy), —N($C_{1-4}$ alkyl)C(O)($C_{1-4}$ alkyl), —N($C_{1-4}$ alkyl)C(O)($C_{1-4}$ alkoxy), —OC(O) ($C_{1-4}$ alkyl), —OC(O)($C_{1-4}$ alkoxy), —Si($C_{1-4}$ alkyl)$_3$, —Si($C_{1-4}$ alkoxy)$_3$, $C_{6-10}$aryl, $C_{6-10}$aryloxy, $C_{6-10}$arylthio, $C_{6-10}$heteroaryl, —($C_{1-8}$-perhaloalkyl), aryl$C_{2-6}$alkynyl, —$C_{2-6}$alkenyl, heteroaryl$C_{2-6}$alkynyl, —$C_{2-6}$alkenyl, $C_{3-8}$cycloalkyl, —NR$^8$R$^9$ where R$^8$ and R$^9$ are independently H, —$C_{1-4}$ alkyl-$C_{2-4}$alkenyl, —$C_{2-4}$alkynyl or combine with the interjacent nitrogen to form a five- or six-membered ring which may comprise one or two or three heteroatoms (one or two N, O or S atoms in addition to the interjacent nitrogen atom), in which case the heterocyclic ring is unsubstituted or the heterocyclic ring is substituted by one or two oxo substituent, $C_{1-4}$alkyl groups, —$C_{2-4}$alkenyl or substituted —$C_{2-4}$ alkenyl, —$C_{2-4}$alkynyl or substituted —$C_{2-4}$alkynyl, —C(O)H, —C(O)($C_{1-4}$ alkyl), —C(O)($C_{1-4}$ alkoxy), —C(O)NH$_2$, —C(O)NH($C_{1-4}$ alkyl), —C(O)N($C_{1-4}$ alkyl)($C_{1-4}$ alkyl), —OC(O)NH($C_{1-4}$ alkyl), —OC(O)N($C_{1-4}$ alkyl)($C_{1-4}$ alkyl), —NHC(O)($C_{1-4}$ alkyl), —NHC(O)($C_{1-4}$ alkoxy), —N($C_{1-4}$alkyl)C(O)($C_{1-4}$ alkyl), —N($C_{1-4}$alkyl)C(O)($C_{1-4}$ alkoxy), —OC(O) ($C_{1-4}$alkyl), —OC(O)($C_{1-4}$ alkoxy), —Si($C_{1-4}$alkyl)$_3$, —Si($C_{1-4}$alkoxy)$_3$, $C_{6-10}$aryl, $C_{6-10}$aryloxy, $C_{6-10}$arylthio, $C_{6-10}$heteroaryl, —($C_{1-8}$-perhaloalkyl), aryl$C_{1-4}$alkynyl, —$C_{1-6}$alkynyl, wherein all the alkyl, alkenyl, alkynyl, alkoxy, aryl, aryloxy, arylthio or heteroaryl groups are either substituted or unsubstituted, preferably these substituents of the substituted groups bear only one further substituent, more preferably these substituents of the substituted groups are not further substituted.

The more preferred substituents of the substituted alkyl groups, alkenyl groups, the alkynyl groups and the alkoxy are selected from the following substituents —OH, CN, F, Cl, $C_{1-4}$alkoxy, —$C_{1-4}$alkoxy, —$C_{1-4}$alkylthio, $C_{1-4}$alkyl, $C_{2-4}$alkenyl, $C_{2-4}$alkenyl, $C_{2-4}$alkinyl, $C_{6-10}$aryl, —$C_{1-4}$alkylamino, —OC(O) ($C_{1-4}$alkyl)-C(O)($C_{1-4}$alkoxy). The alkyl groups are branched or linear. The most preferred alkyl groups are methyl, ethyl, propyl, iso-propyl, n-butyl, t-butyl (1,1-dimethylethyl), sec-butyl (1-methylpropyl), iso-butyl (2-methylpropyl), pentyl, iso-pentyl (3-methylbutyl, iso-amyl), 1-methylpentyl, 1-ethylpentyl, hexyl, heptyl, or octyl. Preferred alkenyl groups are ethenyl, propenyl (1-propenyl, 2-propenyl), butenyl (1-butenyl, 2-butenyl, 3-butenyl, 2-methylpropen-1-yl, 2-methylpropen-2-yl), pentenyl (pent-1-enyl, pent-2-enyl, pent-3-enyl, 2-methylbut-1-enyl, 3-methylbut-1-enyl, 2-methylbut-2-enyl, 3-methylbut-2-enyl, 2-methylbut-3-enyl, 3-methylbut-3-enyl, 1,2-dimethylprop-2-enyl, 1,1-dimethylprop-2-enyl). Preferred alkynyl groups are ethinyl, propinyl (prop-1-inyl or prop-2-inyl (propargyl)), butyl (but-1-ynyl, but-2-ynyl, but-3-ynyl), pentinyl (pent-1-inyl, pent-2-inyl, pent-3-inyl, pent-4-yl, 3-methylbut-1-inyl, 2-methylbut-3-inyl, 1-methylbut-3-inyl). The most preferred alkyl groups and the most preferred alkoxy groups are methyl, ethyl, propyl, t-buyl, methoxy and ethoxy groups. Methyl, ethyl and methoxy groups are very particularly preferred.

Preferably the alkyl groups in the compound of formula (I) and/or the alkoxy groups in the compound of formula (I) bear not more than two further substituents, more preferably the alkyl groups in the compound of formula (I) and/or the alkoxy groups in the compound of formula (I) bear not more than one further substituent, most preferred the alkyl groups in the compound of formula (I) and/or the alkoxy groups in the compound of formula (I) are not further substituted.

The aryl and hetero aryl groups are either substituted or unsubstituted 5-membered or 6-membered aromatic monocyclic which may contain at least one heteroatom selected from N, S, O or unsubstituted or substituted 9-membered or 10-membered aromatic bicyclic ring system which may contain one or two heteroatoms selected from N, S, O.

Preferrably the unsubstituted or substituted heteroaryl which is mono cyclic or bicyclic ring system which is five to ten membered containing at least one heteroatom selected from O, N or S and has not more than 3 heteroatoms For examples of such groups include furyl, thienyl, pyrrolyl, pyrazolyl, imidazolyl, 1,2,3-triazolyl, 1,2,4-triazolyl, 1,3,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, preferably thiazolyl, imidazolyl, pyrrazolyl, pyridyl and pyrimidinyl The aryl groups and heteroaryl groups are preferably unsubstituted or substituted 5-membered or 6-membered aromatic monocyclic ring system which may contain one or two heteroatoms selected from N or S or O wherein the substituents are selected from the group consisting of halogen, hydroxy, $C_1$-$C_4$alkyl, $C_1$-$C_4$haloalkyl, $C_1$-$C_4$alkoxy, $C_1$-$C_4$alkylthio, $C_1$-$C_4$alkoxy-$C_1$-$C_4$alkyl, $C_1$-$C_4$haloalkoxy, $C_1$-$C_4$alkoximino and $C_1$-$C_4$alkylendioxy groups, phenyl, pyridyl, thiophene, imidazole or pyrrazol groups The aryl groups and heteroaryl groups are preferably unsubstituted or substituted 9-membered or 10-membered aromatic bicyclic ring system which may contain one or two heteroatoms selected from N or S or O wherein the substituents are selected from the group consisting of halogen, hydroxy, $C_1$-$C_4$alkyl, $C_1$-$C_4$haloalkyl, $C_1$-$C_4$alkoxy, $C_1$-$C_4$alkylthio, $C_1$-$C_4$alkoxy-$C_1$-$C_4$alkyl, $C_1$-$C_4$haloalkoxy, $C_1$-$C_4$alkoximino and $C_1$-$C_4$alkylendioxy groups, more preferably naphtyl, benzofuranyl, purinyl, indolyl, benzo[b]thiophenyl or quinolinyl groups The preferred substituents of the substituted aryl groups and heteroaryl groups in the compound of formula (I) are selected from the group consisting of halogen, hydroxy, cyano, nitro, —C(O)($C_{1-4}$ alkoxy), —C(O)($C_{1-4}$ alkyl), —C(O)—NH—($C_{1-4}$ alkyl), —C(O)—N($C_{1-4}$ alkyl)$_2$, $C_1$-$C_4$alkyl, $C_1$-$C_4$haloalkyl, $C_1$-$C_4$alkoxy, $C_1$-$C_4$alkylthio, $C_1$-$C_4$alkoxy-$C_1$-$C_4$alkyl, $C_1$-$C_4$haloalkoxy, $C_1$-$C_4$alkoximino, $C_1$-$C_4$alkylendioxy, —C(O)NH($C_{1-4}$ alkyl), —C(O)N($C_{1-4}$ alkyl)($C_{1-4}$ alkyl), —OC(O)NH($C_{1-4}$ alkyl), —OC(O)N($C_{1-4}$ alkyl)($C_{1-4}$ alkyl), —NHC(O)($C_{1-4}$ alkyl), —NHC(O)($C_{1-4}$ alkoxy), —N($C_{1-4}$alkyl)C(O)($C_{1-4}$ alkyl), —N($C_{1-4}$ alkyl)C(O)($C_{1-4}$ alkoxy), —OC(O) ($C_{1-4}$ alkyl), more preferred substituents of the substituted aryl groups or heteroaryl groups in the compound of formula (I) are selected from the following substituents F, Cl, $CF_3$, CN, —OH, nitro, —$C_{1-4}$ alkyl, —$C_{1-4}$ alkoxy, —C(O)($C_{1-4}$ alkoxy), —C(O)H, —C(O)($C_{1-4}$ Alkyl), —wherein the alkyl groups are either substituted or unsubstituted.

The most preferred substituents of the substituted aryl groups and heteroaryl groups in the compound of formula (I) are selected from the following substituents, F, Cl, —$C_{1-4}$ Alkyl, $C_{1-4}$alkoxy, —CN, —C(O)($C_{1-4}$ alkoxy), —C(O)($C_{1-4}$ alkyl), —C(O)—N—($C_{1-4}$ alkyl) and preferably F, Cl are the even more preferred substituents of the substituted aryl groups in the compound of formula (I).

In a further aspect the present invention relates to compounds of formula (I)

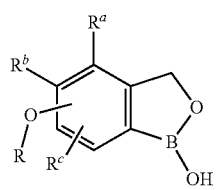

(I)

wherein $R^a$ and $R^b$ and $R^c$ independently are H, fluorine, chlorine, bromine, cyano, nitro, unsubstituted or substituted $C_1$-$C_6$alkyl or unsubstituted or substituted $C_1$-$C_6$haloalkyl, unsubstituted or substituted $C_1$-$C_6$alkoxy, unsubstituted or substituted $C_1$-$C_6$haloalkoxy, unsubstituted or substituted $C_2$-$C_6$alkenyl, unsubstituted or substituted $C_2$-$C_6$alkynyl;

R is H, unsubstituted or substituted $C_1$-$C_6$alkyl, unsubstituted or substituted $C_1$-$C_6$haloalkyl, unsubstituted or substituted with five to ten ring membered aryl-A-, unsubstituted or substituted heteroaryl with 5 to 7 ring members comprising heteroatoms selected form O, S and N, unsubstituted or substituted $C_3$-$C_6$cycloalkyl, unsubstituted or substituted $C_3$-$C_6$heterocycloalkyl ring members comprising heteroatoms selected form O, S and N, $C_2$-$C_6$alkenyl, $C_2$-$C_6$alkynyl, C(O)R', C(O)OR', S(O)$_n$R'

R' is H, unsubstituted or substituted $C_1$-$C_6$alkyl, unsubstituted or substituted $C_1$-$C_6$haloalkyl, unsubstituted or substituted aryl, unsubstituted or substituted heteroaryl n is an integer 0 to 2;

A is a bridging element selected from —$C_{1-4}$alkylene, —C(O)—, $C_{1-4}$alkylene-C(O)—, —C(O)—$C_{1-4}$alkylene wherein the alkylene bridges may be unsubstituted or substituted like an alkyl group;

or if the moiety O—R is in the position 6 and the substituent $R^c$ is in the position 7R forms a 5 to 7 membered ring with either $R^b$ or $R^c$ and this 5 to 7 membered ring may contain further heteroatoms selected form O, S and N; or if the moiety O—R is in the position 7 and the substituent $R^c$ is in the position 6R forms a 5 to 7 membered ring with $R^c$ and this 5 to 7 membered ring may contain further heteroatoms selected form O, S and N;

wherein the substituents for the aryl, heteroaryl, are independently selected from the group consisting of halogen, hydroxy, cyano, nitro, $C_1$-$C_6$alkyl, $C_1$-$C_6$haloalkyl, $C_1$-$C_6$alkoxy, $C_1$-$C_6$alkoxy-$C_1$-$C_6$alkyl, $C_1$-$C_6$haloalkoxy, $C_1$-$C_6$alkoximino and $C_1$-$C_6$alkylendioxy, C(O)($C_{1-4}$ alkoxy), —C(O)($C_{1-4}$ alkyl), —C(O)—NH—($C_{1-4}$ alkyl), —C(O)—N($C_{1-4}$ alkyl)$_2$, —C(O)H, —C(O)OH and wherein the substituents for the cycloalkyl, heterocycloalkyl, alkyl, alkenyl and alkynyl moieties are independently selected from —OH, CN, NO$_2$, F, Cl, Br, $C_{1-4}$alkyl, $C_{1-4}$alkoxy, —S(O)$_2$OH, —S(O)$_2$$C_{1-4}$alkyl, —C(O)($C_{1-4}$ alkoxy), —OC(O)($C_{1-4}$ alkyl), —C(O)($C_{1-4}$ alkyl), —C(O) ($C_{1-4}$ alkyl)($C_{1-4}$ alkoxy), —C(O)—NH—($C_{1-4}$ alkyl), —C(O)—N($C_{1-4}$ alkyl)$_2$-NH$_2$, $C_{1-4}$alkylamino, di($C_{1-4}$alkylamino), unsubstituted or substituted $C_3$-$C_6$heterocycloalkyl ring members comprising heteroatoms selected form O, S and N;

and agronomically acceptable salts, stereoisomers, diastereoisomers, enantiomers, tautomers, atriopisomers and N-oxides of those compounds.

Preferred values of $R^a$, $R^b$, $R^c$, R and R' are, in any combination (including combinations of preferred values with the original values) as set out below.

Preferably $R^a$ and $R^b$ and $R^c$ independently are H, fluorine, chlorine, bromine, nitro, unsubstituted or substituted $C_1$-$C_6$alkyl or unsubstituted or substituted $C_1$-$C_6$haloalkyl, unsubstituted or substituted $C_1$-$C_6$alkoxy;

R is H, unsubstituted or substituted $C_1$-$C_6$alkyl, unsubstituted or substituted $C_1$-$C_6$haloalkyl, unsubstituted or substituted with five to ten ring membered aryl-A-, unsubstituted or substituted heteroaryl with 5 to 7 ring members comprising heteroatoms selected form O, S and N, $C_2$-$C_6$alkenyl, $C_2$-$C_6$alkynyl, C(O)R', C(O)OR', S(O)$_n$R'

R' is H, unsubstituted or substituted $C_1$-$C_6$alkyl, unsubstituted or substituted $C_1$-$C_6$haloalkyl, unsubstituted or substituted aryl, unsubstituted or substituted heteroaryl n is an integer 0 to 2;

A is a bridging element selected from —$C_{1-4}$alkylene, —C(O)—, $C_{1-4}$alkylene-C(O)—, —C(O)—$C_{1-4}$alkylene wherein the alkylene bridges may be unsubstituted or substituted like an alkyl group;

or if the moiety O—R is in the position 6 and the substituent $R^c$ is in the position 7R forms a 5 to 7 membered ring with either $R^b$ or $R^c$ and this 5 to 7 membered ring may contain further heteroatoms selected form O, S and N; or if the moiety O—R is in the position 7 and the substituent $R^c$ is in the position 6R forms a 5 to 7 membered ring with $R^c$ and this 5 to 7 membered ring may contain further heteroatoms selected form O, S and N;

wherein the substituents for the aryl, heteroaryl, are independently selected from the group consisting of halogen, hydroxy, cyano, nitro, $C_1$-$C_6$alkyl, $C_1$-$C_6$haloalkyl, $C_1$-$C_6$alkoxy, $C_1$-$C_6$alkoxy-$C_1$-$C_6$alkyl, $C_1$-$C_6$haloalkoxy, $C_1$-$C_6$alkoximino and $C_1$-$C_6$alkylendioxy, —C(O)($C_{1-4}$ alkoxy), —C(O)($C_{1-4}$ alkyl), —C(O)—NH—($C_{1-4}$ alkyl), —C(O)—N($C_{1-4}$ alkyl)$_2$, —C(O)H, —C(O)OH and wherein the substituents for the cycloalkyl, heterocycloalkyl, alkyl, alkenyl and alkynyl moieties are independently selected from —OH, CN, NO$_2$, F, Cl, Br, $C_{1-4}$alkyl, $C_{1-4}$alkoxy, —S(O)$_2$OH, —S(O)$_2$$C_{1-4}$alkyl, —C(O)($C_{1-4}$ alkoxy), —OC(O)($C_{1-4}$ alkyl), —C(O)($C_{1-4}$ alkyl), —C(O) ($C_{1-4}$ alkyl)($C_{1-4}$ alkoxy), —C(O)—NH—($C_{1-4}$ alkyl), —C(O)—N($C_{1-4}$ alkyl)$_2$-NH$_2$, $C_{1-4}$alkylamino, di($C_{1-4}$alkylamino), unsubstituted or substituted $C_3$-$C_6$heterocyloalkyl ring members comprising heteroatoms selected form O, S and N;

More preferably $R^a$ and $R^b$ and $R^c$ independently are H, fluorine, chlorine, bromine, nitro, unsubstituted or substituted $C_1$-$C_6$alkyl or unsubstituted or substituted $C_1$-$C_6$haloalkyl, unsubstituted or substituted $C_1$-$C_6$alkoxy; R is H, unsubstituted or substituted $C_1$-$C_6$alkyl, unsubstituted or substituted $C_1$-$C_6$haloalkyl, unsubstituted or substituted with five to ten ring membered aryl-A-, unsubstituted or substituted heteroaryl with 5 to 7 ring members comprising heteroatoms selected form O, S and N, $C_2$-$C_6$alkenyl, $C_2$-$C_6$alkynyl, C(O)R', C(O)OR', S(O)$_n$R'

R' is H, unsubstituted or substituted $C_1$-$C_6$alkyl, unsubstituted or substituted $C_1$-$C_6$haloalkyl, unsubstituted or substituted aryl, unsubstituted or substituted heteroaryl n is an integer 0 to 2;

A is a bridging element selected from —$C_{1-4}$alkylene, —C(O)—, —C(O)—$C_{1-4}$alkylene wherein the alkylene bridges may be unsubstituted or substituted like an alkyl group;

wherein the substituents for the aryl, heteroaryl, are independently selected from the group consisting of halogen, hydroxy, cyano, nitro, $C_1$-$C_6$alkyl, $C_1$-$C_6$haloalkyl, $C_1$-$C_6$alkoxy, $C_1$-$C_6$alkoxy-$C_1$-$C_6$alkyl, and wherein the substituents for the cycloalkyl, heterocycloalkyl, alkyl, alkenyl and alkynyl moieties are independently selected from —OH, CN, NO$_2$, F, Cl, Br, $C_{1-4}$alkyl, $C_{1-4}$alkoxy, —S(O)$_2$OH, —S(O)$_2$$C_{1-4}$alkyl, —C(O)($C_{1-4}$ alkoxy), —OC(O)($C_{1-4}$ alkyl), —C(O)($C_{1-4}$ alkyl), —C(O) ($C_{1-4}$ alkyl)($C_{1-4}$ alkoxy), unsubstituted or substituted $C_3$-$C_6$heterocyloalkyl ring members comprising heteroatoms selected form O, S and N;

In a preferred embodiment aryl-A- is unsubstituted or substituted benzyl, unsubstituted or substituted phenylcarbonyl, unsubstituted or substituted phenyl-C(O)—$C_{1-4}$alkylene, preferably benzyl, phenylcarbonyl, —C(O)-methylene.

Even more preferably $R^a$ is H;

$R^b$ is fluorine, chlorine, bromine, $C_1$-$C_2$alkoxy or $C_1$-$C_2$ haloalkoxy;

$R^c$=H, fluorine, chlorine, bromine, $C_1$-$C_2$alkoxy or $C_1$-$C_2$ haloalkoxy;

R is ethyl, methyl, propargyl, C(O)R'

R' is $C_2$-$C_6$alkyl or if the moiety O—R is in the position 6 and the substituent $R^c$ is in the position 7R forms a 5 to 7 membered ring with either $R^b$ or $R^c$ and this 5 to 7 membered ring may contain further heteroatoms selected form O, S and N; or if the moiety O—R is in the position 7 and the substituent $R^c$ is in the position 6R forms a 5 to 7 membered ring with $R^c$ and this 5 to 7 membered ring may contain further heteroatoms selected form O, S and N;

Yet even more preferably $R^a$ is H;

$R^b$ is fluorine, chlorine, $C_1$-$C_2$alkoxy or $C_1$-$C_2$ haloalkoxy;

$R^c$=H, fluorine, chlorine, $C_1$-$C_2$alkoxy or $C_1$-$C_2$ haloalkoxy;

R is ethyl, methyl, propargyl, C(O)R';

R' is $C_2$-$C_6$alkyl; or if the moiety O—R is in the position 6 and the substituent $R^c$ is in the position 7R forms a 5 to 7 membered ring with either $R^b$ or $R^c$ and this 5 to 7 membered ring may contain further heteroatoms selected form O; or if the moiety O—R is in the position 7 and the substituent $R^c$ is in the position 6R forms a 5 to 7 membered ring with $R^c$ and this 5 to 7 membered ring may contain further heteroatoms selected form O;

Even more preferably $R^a$ is H;

$R^b$ is fluorine, chlorine;

$R^c$=H, fluorine, chlorine, $C_1$-$C_2$alkoxy or $C_1$-$C_2$ haloalkoxy;

R is ethyl, methyl, propargyl, C(O)R';

R' is $C_2$-$C_6$alkyl.

if the moiety O—R is in the position 6 and the substituent $R^c$ is in the position 7R forms a 5 to 7 membered ring with either $R^b$ or $R^c$ and this 5 to 7 membered ring may contain further heteroatoms selected form O; or if the moiety O—R is in the position 7 and the substituent $R^c$ is in the position 6R forms a 5 to 7 membered ring with $R^c$ and this 5 to 7 membered ring may contain further heteroatoms selected form O;

In a further more preferred embodiment $R^a$ is H;

$R^b$ is fluorine, chlorine;

$R^c$=H, fluorine, chlorine, $C_1$-$C_2$alkoxy or $C_1$-$C_2$ haloalkoxy;

R is ethyl, methyl, propargyl, C(O)R';

R' is $C_2$-$C_6$alkyl.

if the moiety O—R is in the position 6 and the substituent $R^c$ is in the position 7R forms a 5 membered ring with either $R^b$ or $R^c$ and this 5 membered ring may contain further heteroatoms selected form O; or if the moiety O—R is in the position 7 and the substituent $R^c$ is in the position 6R forms a 5 membered ring with $R^c$ and this 5 membered ring may contain further heteroatoms selected form O;

Most preferably $R^a$ is H;

$R^b$ is fluorine, chlorine;

$R^c$=H, fluorine, chlorine;

R is ethyl, methyl, propargyl preferably methyl, ethyl;

In a preferred embodiment of this invention the compounds of formula (I) R does not form a ring with either $R^b$ or $R^c$ In a preferred embodiment of this invention the compounds of formula (I)
$R^a$ is H;
$R^b$ is H, NO$_2$, chlorine, fluoro, methyl, ethyl or forms together with R a ring as follows
$R^c$=H, fluorine, chlorine, bromine;
R is H, C$_{1-5}$-alkyl, C$_{1-5}$-alkylacyl (preferably acetyl), formyl, CH$_2$CN, trifluormethylsulfonyl, methylsulfonyl,
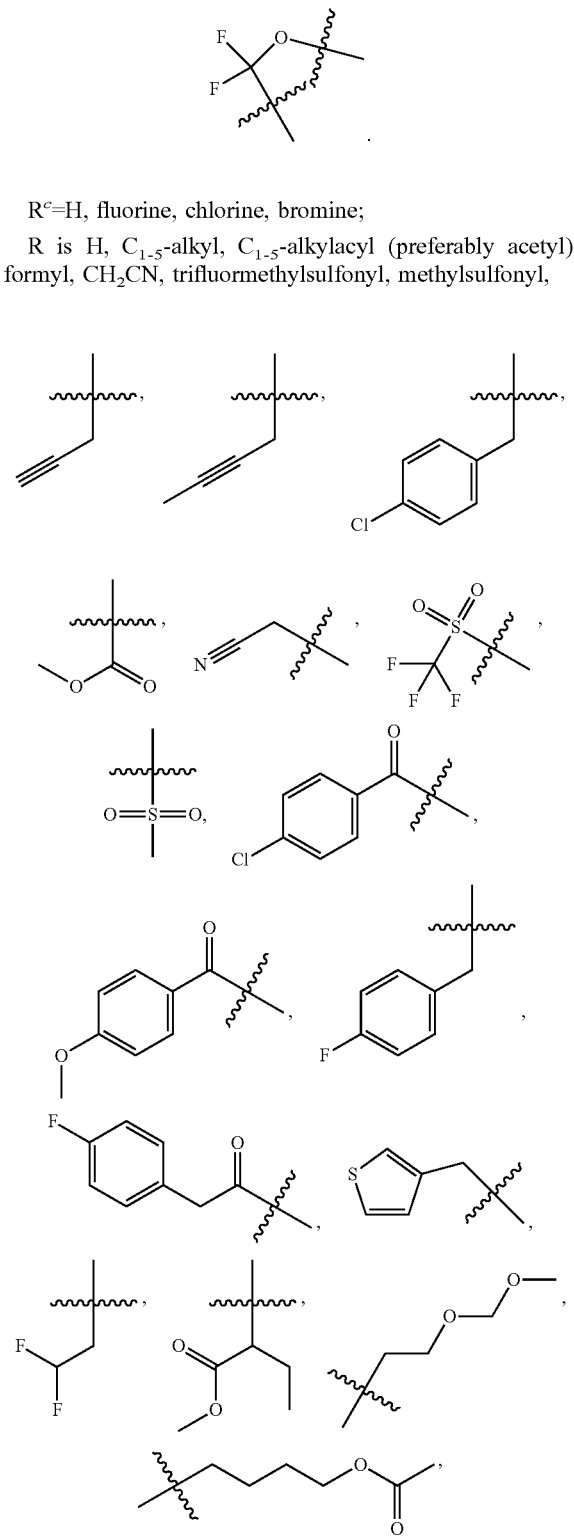
-continued
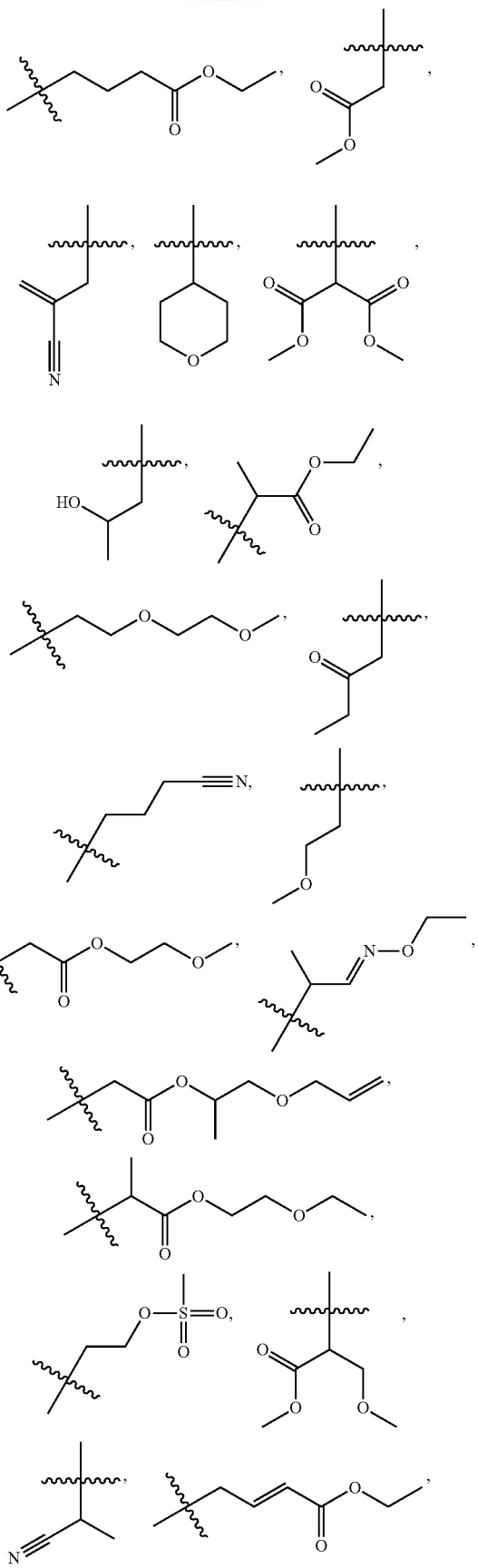

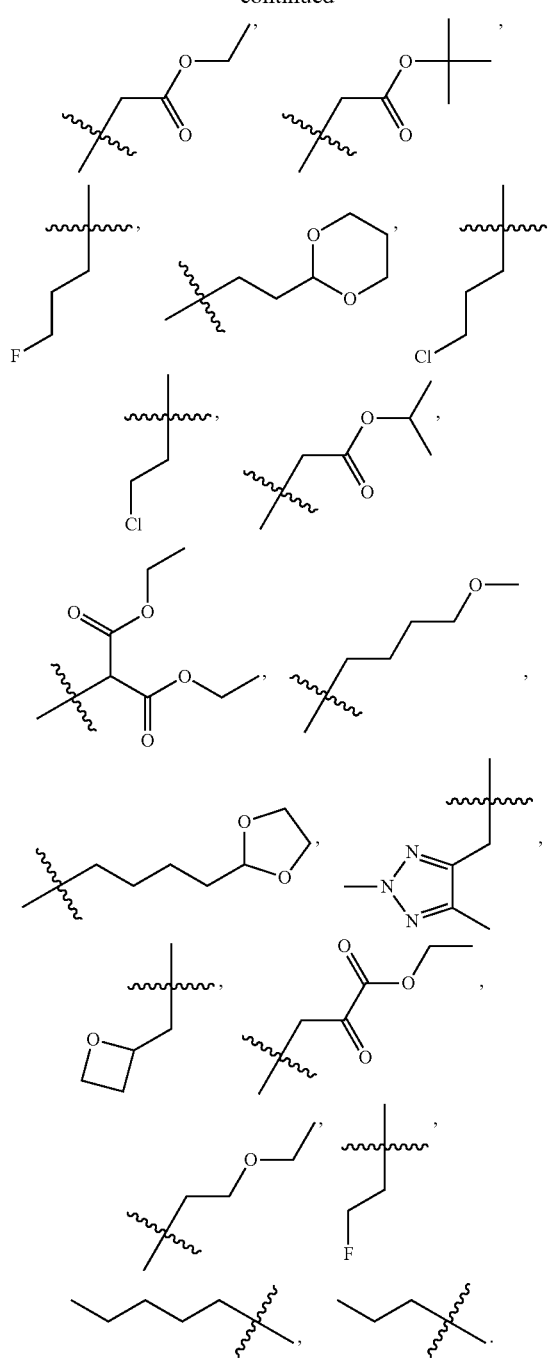
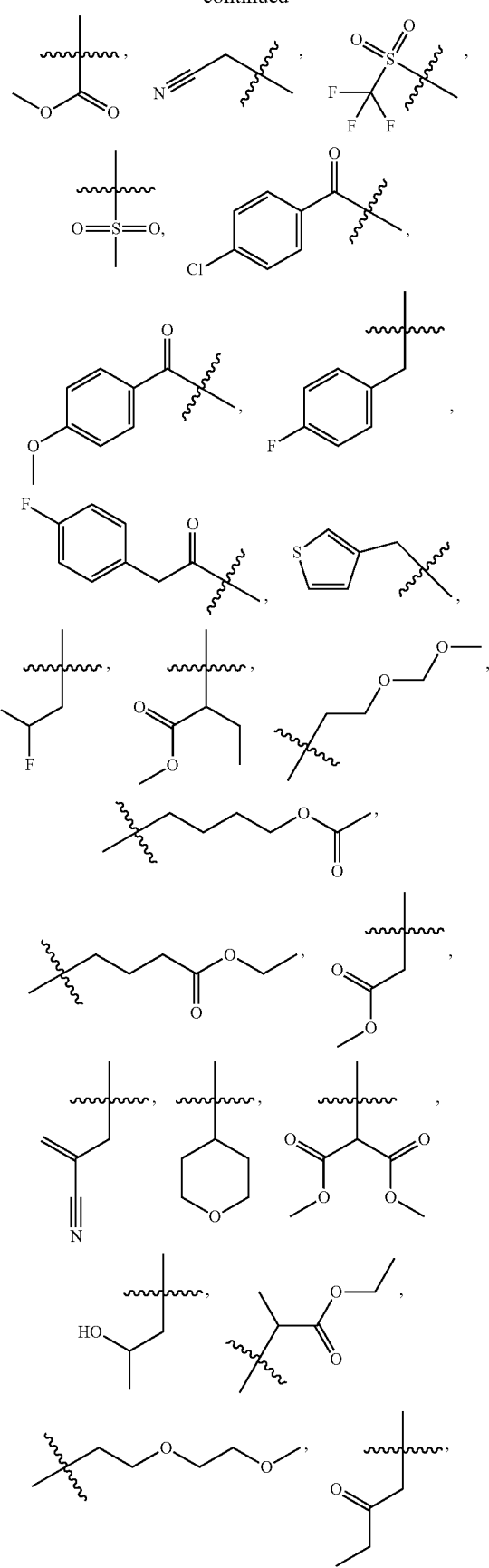
In a preferred embodiment of this invention in the compounds of formula (I) R is R is H, $C_{1-5}$-alkyl, $C_{1-5}$-alkylacyl, formyl, $CH_2CN$, trifluormethylsulfonyl, methylsulfonyl, -continued

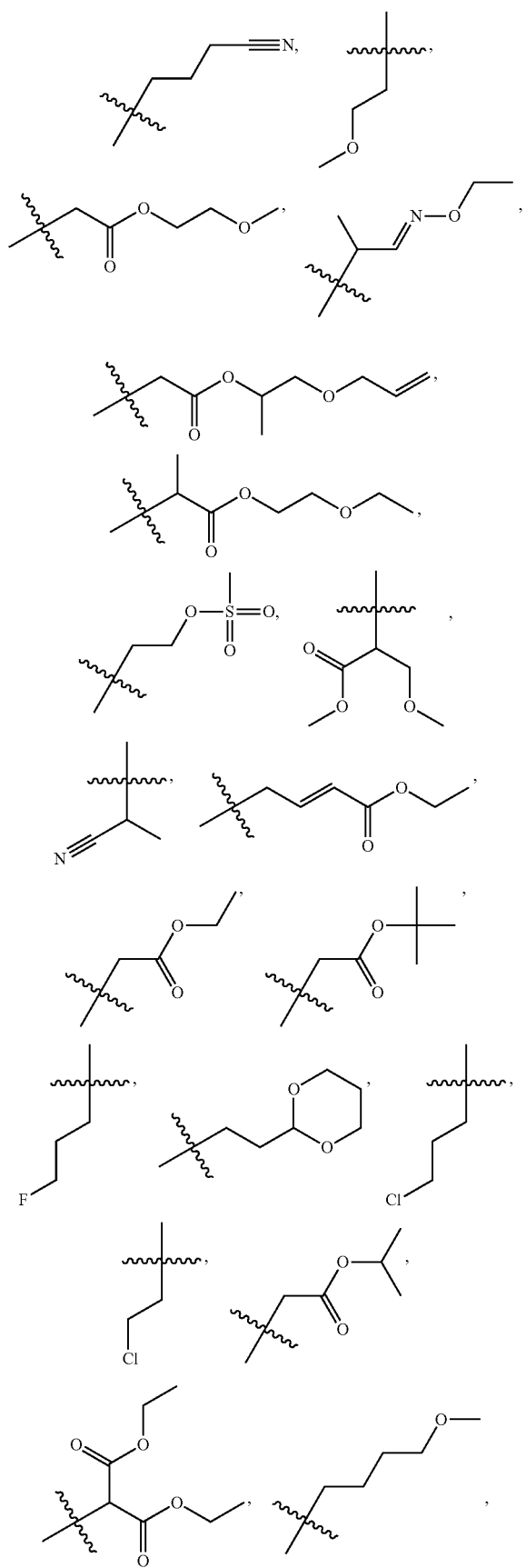

-continued

In a preferred embodiment of this invention the compounds of formula (I) have the formula I-a

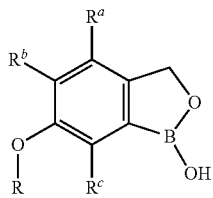

I-a and all the substituents $R^a$, $R^b$, $R^c$, R and R' are as defined above. In the compounds of the formula I-a the substituent $R^a$ is in the position 4, the substituent $R^b$ is in the position 5, the substituent O—R is in the position 6 and the substituent $R^c$ is in the position 7.

In a preferred embodiment of this invention the compounds of formula (I) have the formula I-b

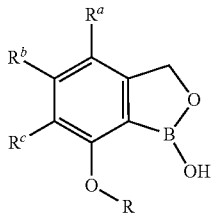

I-b wherein
$R^a$ is H;
$R^b$ is fluorine, chlorine;
$R^c$=H, fluorine, chlorine;
R is H, $C_2$-$C_6$alkyl;
Preferably
$R^a$ is H;
$R^b$ is fluorine, chlorine;
$R^c$=H, fluorine, chlorine;

R is H, $C_2$-$C_6$alkyl, preferably methyl, ethyl;
More preferably
$R^a$ is H;
$R^b$ is fluorine, chlorine, preferably chlorine;
$R^c$=H;
R is H, ethyl, methyl;
Even more preferably
$R^a$ is H;
$R^b$ is fluorine, chlorine, preferably chlorine;
$R^c$=H;
R is ethyl, methyl;
In the compounds of the formula I-b the substituent $R^a$ is in the position 4, the substituent $R^b$ is in the position 5, the substituent O—R is in the position 7 and the substituent $R^c$ is in the position 6.

In a further aspect the present invention relates to compounds of formula (I)

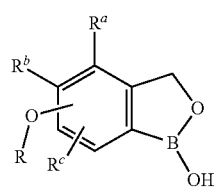
(I)

wherein
$R^a$ and $R^b$ and $R^c$ independently are H, fluorine, chlorine, bromine, cyano, nitro, unsubstituted or substituted $C_1$-$C_6$alkyl or unsubstituted or substituted $C_1$-$C_6$haloalkyl, unsubstituted or substituted $C_1$-$C_6$alkoxy, $C_2$-$C_6$alkenyl, $C_2$-$C_6$alkynyl;

R is H, unsubstituted or substituted $C_1$-$C_6$alkyl, unsubstituted or substituted $C_1$-$C_6$haloalkyl, unsubstituted or substituted aryl, unsubstituted or substituted heteroaryl, unsubstituted or substituted $C_3$-$C_6$cycloalkyl, unsubstituted or substituted $C_1$-$C_6$heteroaycloalkyl, unsubstituted or substituted $C_1$-$C_6$alkoxy, unsubstituted or substituted $C_1$-$C_6$haloalkoxy, $C_2$-$C_6$alkenyl, $C_2$-$C_6$alkynyl, benzyl, C(O)R', C(O)OR', S(O)$_n$R'

R'=unsubstituted or substituted $C_1$-$C_6$alkyl, unsubstituted or substituted $C_1$-$C_6$haloalkyl, unsubstituted or substituted aryl, unsubstituted or substituted heteroaryl n is an integer 0 to 2; or if the moiety O—R is in the position 6 and the substituent $R^c$ is in the position 7R forms a 5 to 7 membered ring with either $R^b$ or $R^c$ and this 5 to 7 membered ring may contain further heteroatoms selected form O, S and N; or if the moiety O—R is in the position 7 and the substituent $R^c$ is in the position 6R forms a 5 to 7 membered ring with $R^c$ and this 5 to 7 membered ring may contain further heteroatoms selected form O, S and N;

wherein the substituents for the aryl, heteroaryl, are independently selected from the group consisting of halogen, hydroxy, cyano, nitro, $C_1$-$C_6$alkyl, $C_1$-$C_6$haloalkyl, $C_1$-$C_6$alkoxy, $C_1$-$C_6$alkoxy-$C_1$-$C_6$alkyl, $C_1$-$C_6$haloalkoxy, $C_1$-$C_6$alkoximino and $C_1$-$C_6$alkylendioxy, C(O)($C_{1-4}$ alkoxy), —C(O)($C_{1-4}$ alkyl), —C(O)—NH—($C_{1-4}$ alkyl), —C(O)—N($C_{1-4}$ alkyl)$_2$, —C(O)H, —C(O)OH and wherein the substituents for the cycloalkyl, heterocycloalkyl, alkyl, alkenyl and alkynyl moieties are independently selected from —OH, CN, NO$_2$, F, Cl, $C_{1-4}$alkoxy, —C(O)($C_{1-4}$ alkoxy), —C(O)($C_{1-4}$ alkyl), —C(O)—NH—($C_{1-4}$ alkyl), —C(O)—N($C_{1-4}$ alkyl)$_2$ and $C_{1-4}$alkylamino;

and agronomically acceptable salts, stereoisomers, diastereoisomers, enantiomers, tautomers, atriopisomers and N-oxides of those compounds.

In all compounds shown in the schemes below $R^a$, $R^b$, $R^c$, R and R' are as defined above.

Compounds described in the present invention can be prepared using commercially available starting materials or known intermediates using synthetic methods known in the art or described herein.

The following general chemistry routes were used as indicated in generating the examples and can be applied, using the knowledge of one of skill in the art, to other appropriate compounds to obtain additional analogues Compounds of formula I may be prepared by reacting a compound of formula II

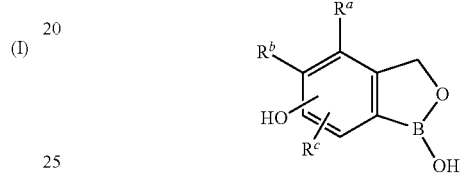
II wherein $R^a$, $R^b$ and $R^c$ are as defined under formula I;
with a compound of formula III-A and III-B

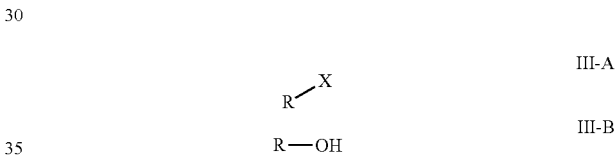

in which R is as defined under formula I,

A further aspect of the present application relates to a compounds selected from the Tables 1-1 to 1-21 and Table 2, preferably the present application relates to a compounds selected from the Table 2.

Yet a further aspect of the present application relates to a single compound selected from the Tables 1-1 to 1-21 and Table 2, preferably the present application relates to a single compound selected from the Table 2.

Yet a further aspect of the present application relates to the compounds from the Tables 1-1 to 1-21 and selected from the Table 2, preferably the present application relates to the compounds from the Table 2.

Compounds of formula I can be prepared by using the synthetic methods described herein. The Scheme-1, Scheme-2, Scheme-3, Scheme-4 and Scheme-5 describes the general synthetic route for the preparation of the compounds of formula I-a and I-b Scheme-1

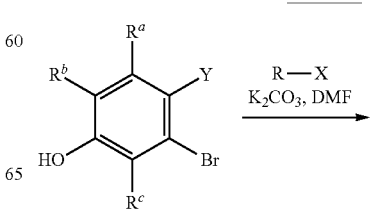

21
-continued
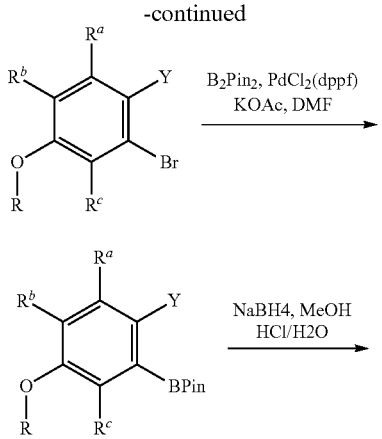
Y = CHO, CO₂R'; wherein R' is C1-C6 alkyl
X = halogen
22
-continued
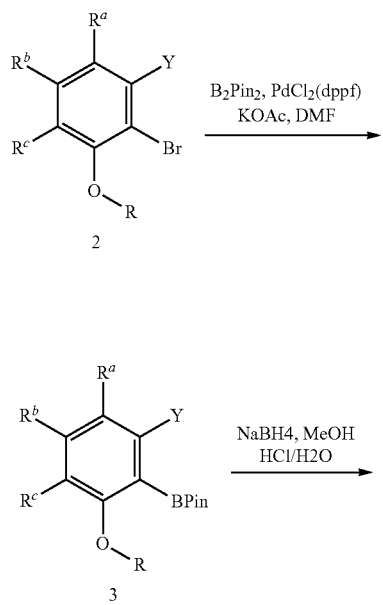
Scheme-2
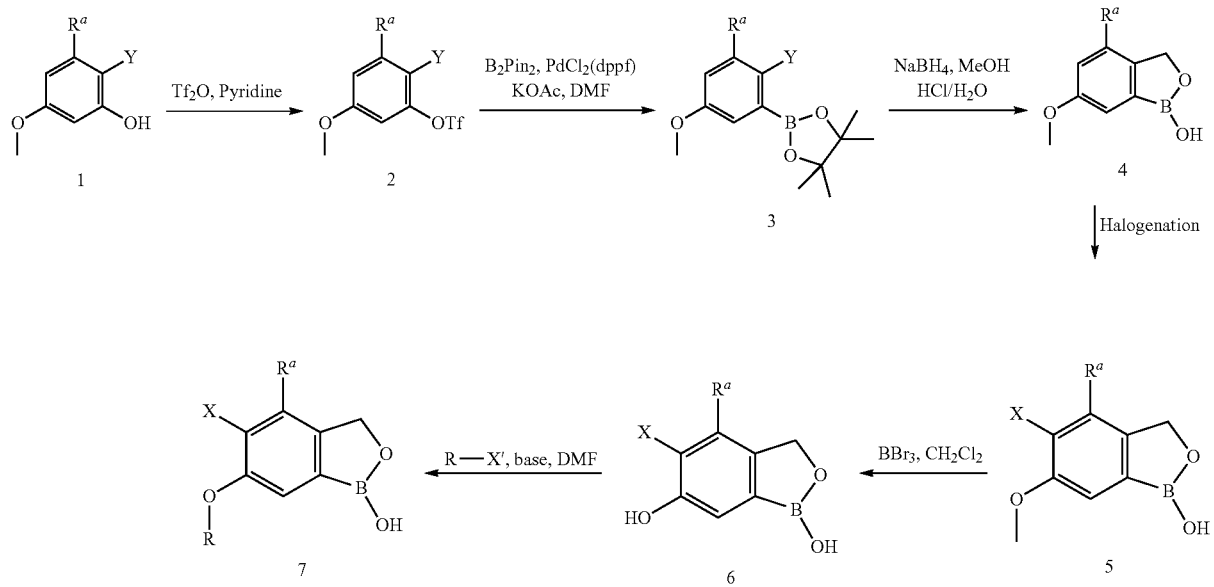
Scheme-3
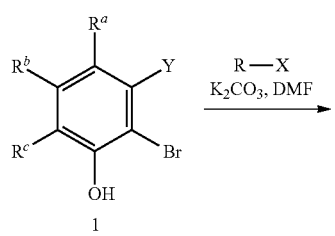
-continued
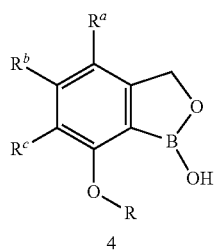
Y = CHO, CO₂R'; wherein R' is C1-C6 alkyl
X = halogen Scheme-4
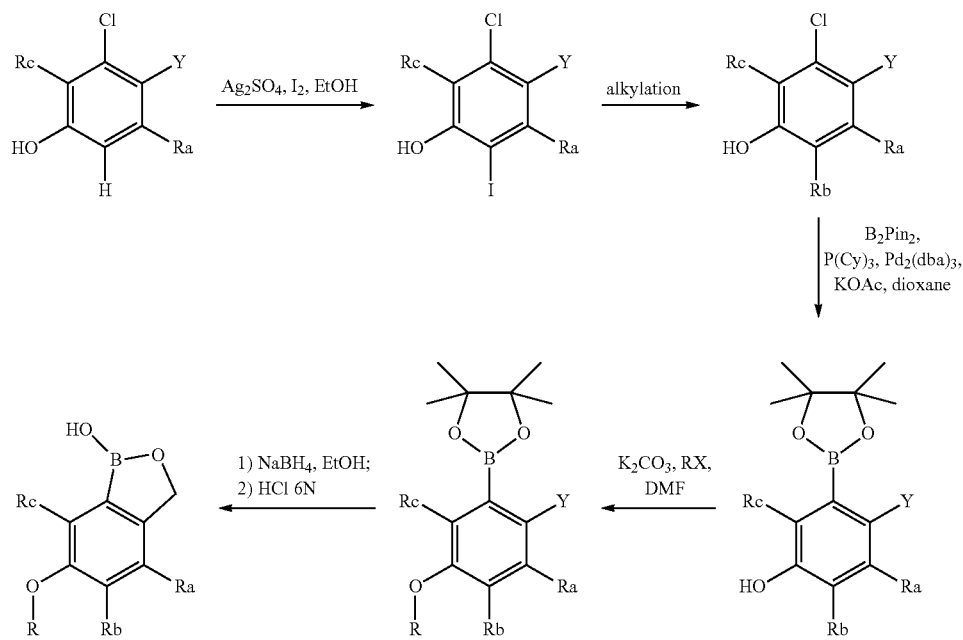
$R^b$ = $C_1$-$C_6$ alkyl
alkylation: for example: ($R^b$)$_3$B$_3$O$_3$ or $R^b$B(OH)$_2$ or $R^b$BPin; Pd catalyst/ligand; base; solvent.
R = $C_1$-$C_6$ alkyl
X = halogen
Y = CO$_2$R′; wherein R′ = $C_1$-$C_6$ alkyl
Scheme-5
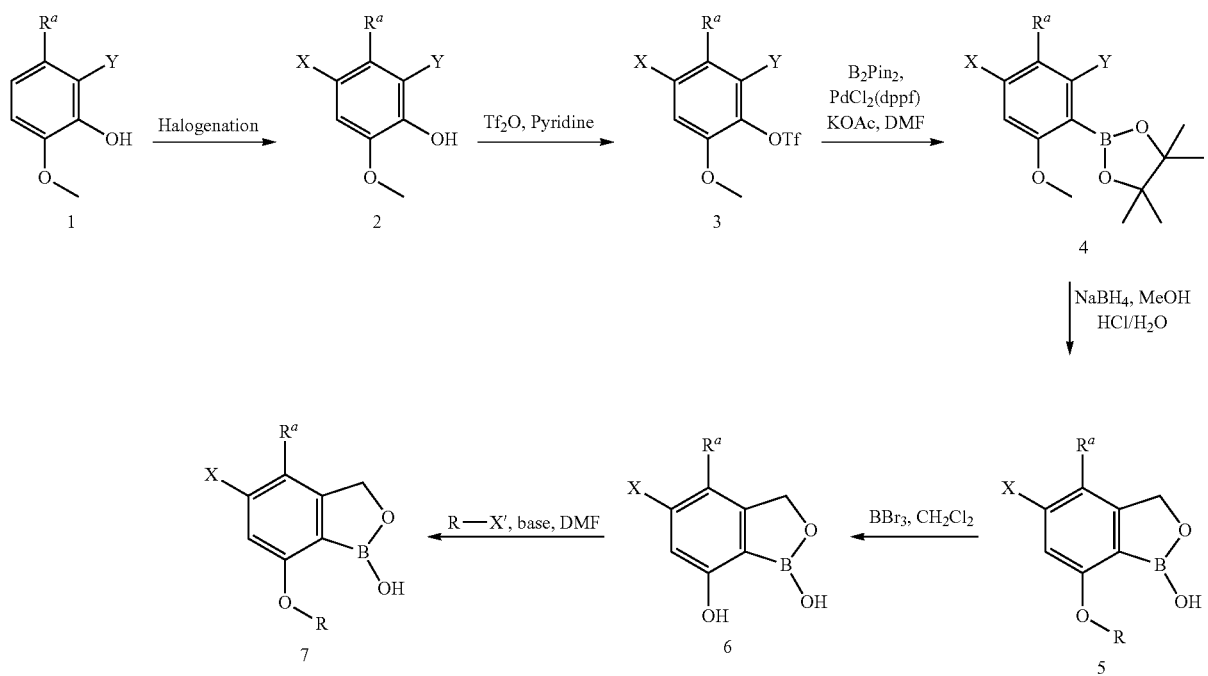

The following tables 1-1 to 1-21 disclose specific compounds of the formula I-a:

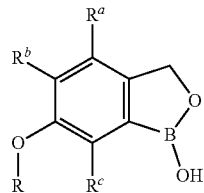

TABLE P

| | R |
|---|---|
| 1 | H |
| 2 | methyl |
| 3 | ethyl |
| 4 | acetyl |
| 5 | formyl |
| 6 | CH$_2$CN |
| 7 | trifluormethylsulfonyl |
| 8 | methylsulfonyl |
| 9 | [propargyl group] |
| 10 | [but-2-ynyl group] |
| 11 | [4-chlorobenzyl group] |
| 12 | [methyl propanoate group] |
| 13 | [cyanomethyl group] |
| 14 | [trifluoromethylsulfonyl group] |
| 15 | [methylsulfonyl group] |

TABLE P-continued

| | R |
|---|---|
| 16 | [4-fluorobenzoyl group] |
| 17 | [4-methoxybenzoyl group] |
| 18 | [4-fluorobenzyl group] |
| 19 | [4-fluorophenylacetyl group] |
| 20 | [thiophen-3-ylmethyl group] |
| 21 | [2,2-difluoroethyl group] |
| 22 | [methyl 2-ethylpropanoate group] |
| 23 | [methoxymethoxyethyl group] |
| 24 | [4-acetoxybutyl group] |
| 25 | [ethyl butanoate group] |

TABLE P-continued
| | R |
|---|---|
| 26 | 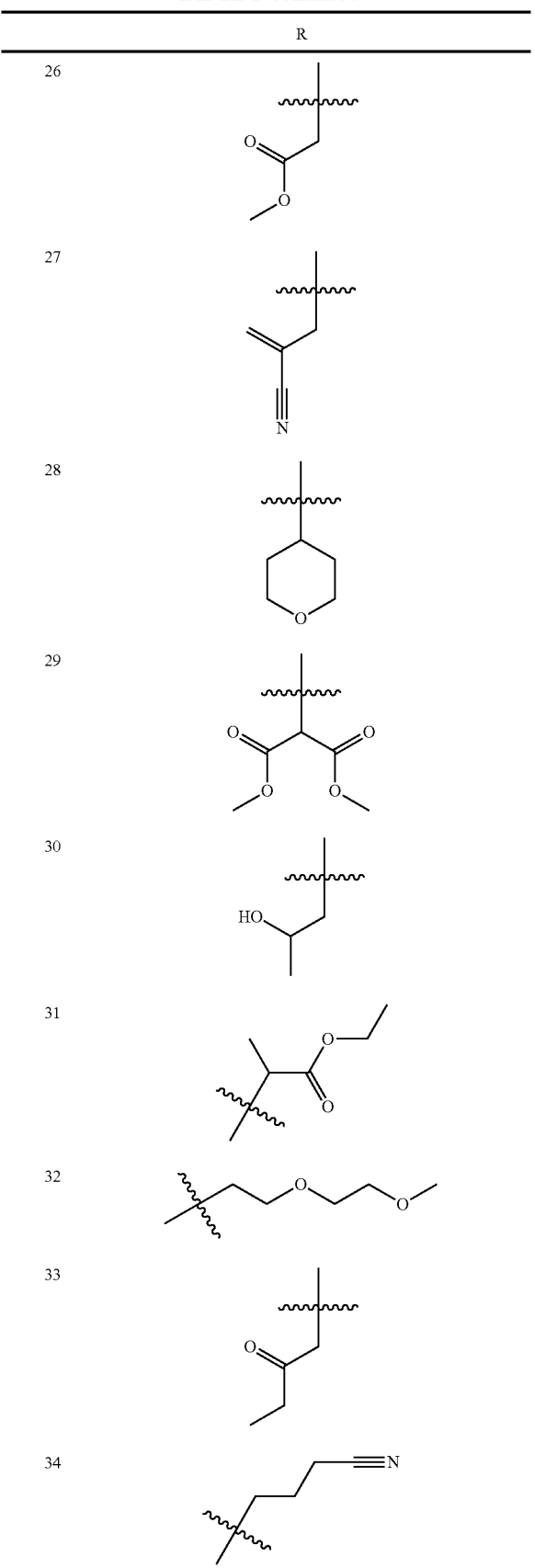 |
| 27 | |
| 28 | |
| 29 | |
| 30 | |
| 31 | |
| 32 | |
| 33 | |
| 34 | |
TABLE P-continued
| | R |
|---|---|
| 35 | 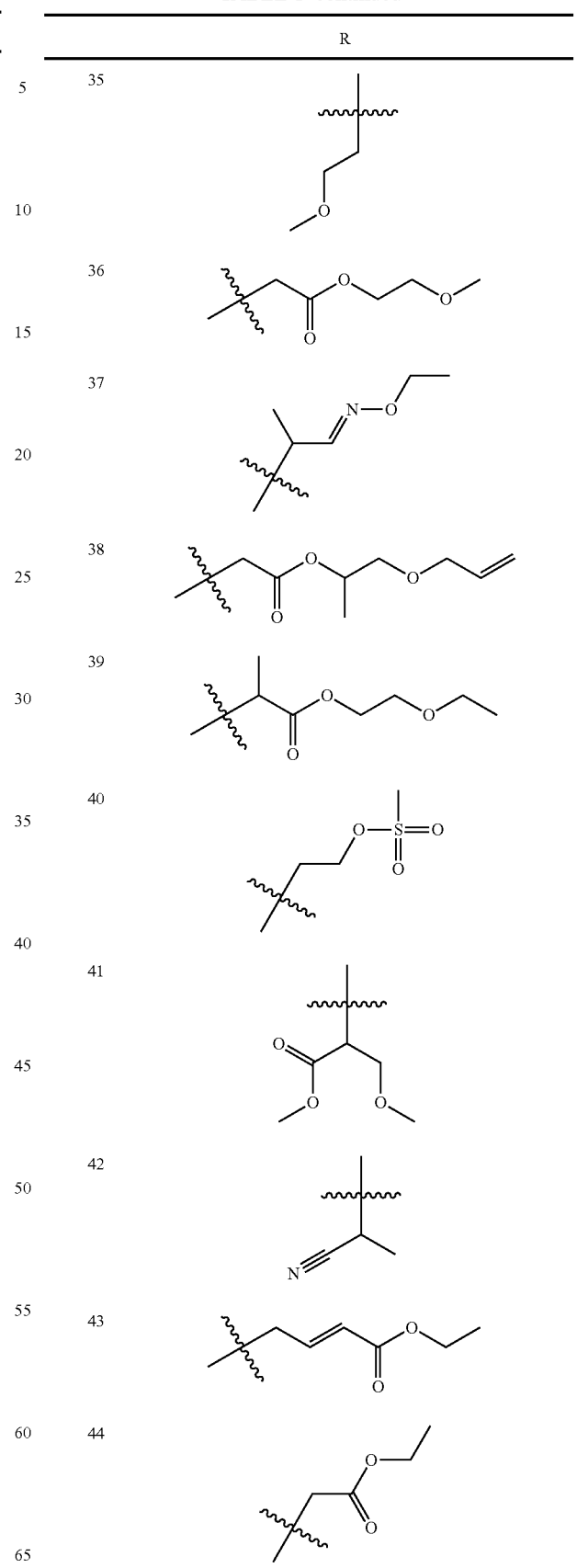 |
| 36 | |
| 37 | |
| 38 | |
| 39 | |
| 40 | |
| 41 | |
| 42 | |
| 43 | |
| 44 | |

TABLE P-continued

| | R |
|---|---|
| 45 | 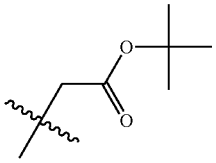 [SMILES: *CC(=O)OC(C)(C)C] |
| 46 | 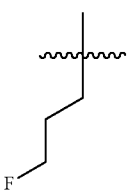 [SMILES: *CCCF] |
| 47 | 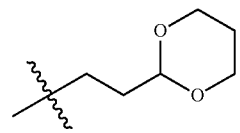 [SMILES: *CCC1OCCCO1] |
| 48 | 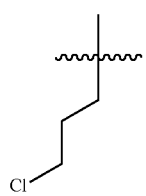 [SMILES: *CCCCl] |
| 49 | 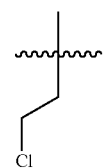 |
| 50 | 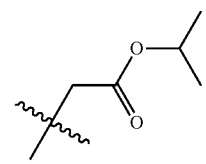 [SMILES: *CC(=O)OC(C)C] |
| 51 | 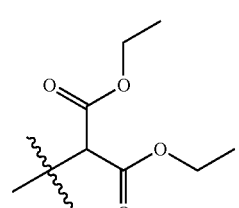 |
| 52 | 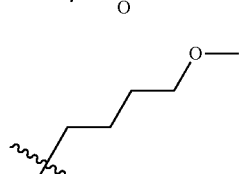 |
| 53 | 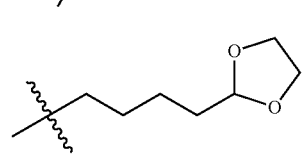 |
| 54 | 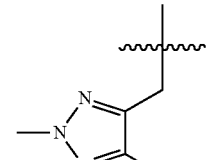 |
| 55 | 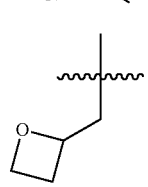 |
| 56 | 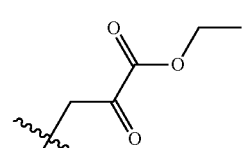 |
| 57 | 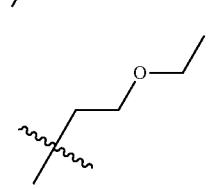 |
| 58 | 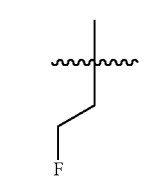 |
| 59 | 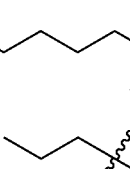 |
| 60 | 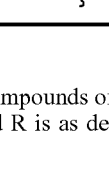 |

Table 1-1

Table 1-1 provides 60 compounds of formula I-a wherein Rb is methyl, Rc is H, and R is as defined in Table P.

Table 1-2

Table 1-2 provides 60 compounds of formula I-a wherein Rb is ethyl, Rc is H, and R is as defined in Table P.

Table 1-3

Table 1-3 provides 60 compounds of formula I-a wherein Rb is F, Rc is H, and R is as defined in Table P.

Table 1-4

Table 1-4 provides 60 compounds of formula I-a wherein Rb is Cl, Rc is H, and R is as defined in Table P.

Table 1-5

Table 1-5 provides 60 compounds of formula I-a wherein Rb is nitro, Rc is H, and R is as defined in Table P.

Table 1-6

Table 1-6 provides 60 compounds of formula I-a wherein Rb is CN, Rc is H, and R is as defined in Table P.

Table 1-7

Table 1-7 provides 60 compounds of formula I-a wherein Rb is CF3, Rc is H, and R is as defined in Table P.

Table 1-8

Table 1-8 provides 60 compounds of formula I-a wherein Rb is methyl, Rc is F, and R is as defined in Table P.

Table 1-9

Table 1-9 provides 60 compounds of formula I-a wherein Rb is ethyl, Rc is F, and R is as defined in Table P.

Table 1-10

Table 1-10 provides 60 compounds of formula I-a wherein Rb is F, Rc is F, and R is as defined in Table P.

Table 1-11

Table 1-11 provides 60 compounds of formula I-a wherein Rb is Cl, Rc is F, and R is as defined in Table P.

Table 1-12

Table 1-12 provides 60 compounds of formula I-a wherein Rb is nitro, Rc is F, and R is as defined in Table P.

Table 1-13

Table 1-13 provides 60 compounds of formula I-a wherein Rb is CN, Rc is F, and R is as defined in Table P.

Table 1-14

Table 1-14 provides 60 compounds of formula I-a wherein Rb is CF3, Rc is F, and R is as defined in Table P.

Table 1-15

Table 1-15 provides 60 compounds of formula I-a wherein Rb is methyl, Rc is Cl, and R is as defined in Table P.

Table 1-16

Table 1-16 provides 60 compounds of formula I-a wherein Rb is ethyl, Rc is Cl, and R is as defined in Table P.

Table 1-17

Table 1-17 provides 60 compounds of formula I-a wherein Rb is F, Rc is Cl, and R is as defined in Table P.

Table 1-18

Table 1-18 provides 60 compounds of formula I-a wherein Rb is Cl, Rc is Cl, and R is as defined in Table P.

Table 1-19

Table 1-19 provides 60 compounds of formula I-a wherein Rb is nitro, Rc is Cl, and R is as defined in Table P.

Table 1-20

Table 1-20 provides 60 compounds of formula I-a wherein Rb is CN, Rc is Cl, and R is as defined in Table P.

Table 1-21

Table 1-21 provides 60 compounds of formula I-a wherein Rb is CF3, Rc is Cl, and R is as defined in Table P.

The invention therefore also relates to a method of controlling or preventing infestation of useful plants by phytopathogenic microorganisms, wherein a compound of formula (I) is applied as active ingredient to the plants, to parts thereof or the locus thereof. The compounds of formula (I) according to the invention are distinguished by excellent activity at low rates of application, by being well tolerated by plants and by being environmentally safe. They have very useful curative, preventive and systemic properties and are used for protecting numerous useful plants. The compounds of formula (I) can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula (I) as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore, the compounds of formula (I) according to the invention may be used for controlling fungi in related areas, for example in the protection of technical materials, including wood and wood related technical products, in food storage or in hygiene management.

The methods according to the instant invention are particularly effective to protect useful plants or plant propagation material thereof against phytopathogenic fungi belonging to the following classes: Ascomycetes (e.g. the genus *Cochliobolus, Colletotrichum, Fusarium, Gaeumannomyces, Giberella, Monographella, Microdochium, Penicillium, Phoma, Pyricularia, Magnaporthe, Septoria, Pseudocercosporella, Tapesia* and *Thielaviopsis*); Basidiomycetes (e.g. the genus *Phakopsora, Puccinia, Rhizoctonia, Thanatephorus, Sphacelotheca, Tilletia, Typhula* and *Ustilago*); Fungi imperfecti (also known as Deuteromycetes; e.g. the genus *Ascochyta, Diplodia, Erysiphe, Fusarium, Helminthosporium, Phomopsis, Pyrenophora* and *Verticillium*); Oomycetes (e.g. *Aphanomyces, Peronospora, Peronosclerospora, Phytophthora, Plasmopara, Pseudoperonospora, Pythium*); and Zygomycets (e.g. the genus *Rhizopus*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); Yield- Gard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins from *Bacillus cereus* or *Bacillus popilliae*; or insecticidal proteins from *Bacillus thuringiensis*, such as 8-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus;* toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyltransferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO03/018810).

Examples of such toxins or transgenic plants capable of synthesising such toxins are disclosed, for example, in EP-A-0 374 753, WO93/07278, WO95/34656, EP-A-0 427 529, EP-A-451 878 and WO03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula (I) can be used in unmodified form or, preferably, together with carriers and adjuvants conventionally employed in the art of formulation.

Therefore the invention also relates to compositions for controlling and protecting against phytopathogenic microorganisms, comprising a compound of formula (I) and an inert carrier, and to a method of controlling or preventing infestation of useful plants by phytopathogenic microorganisms, wherein a composition, comprising a compound of formula (I) as active ingredient and an inert carrier, is applied to the plants, to parts thereof or the locus thereof.

To this end compounds of formula (I) and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants (auxiliaries) can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) or compositions, comprising a compound of formula (I) as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula (I), or a composition, comprising a compound of formula (I) as active ingredient and an inert carrier, is foliar application. The frequency of application and the rate of application will depend on the risk of infestation by the corresponding pathogen. However, the compounds of formula (I) can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, i.e. a composition comprising the compound of formula (I) and, if desired, a solid or liquid adjuvant or, if desired as well, a further, other biocidally active ingredient, is prepared in a known manner, typically by intimately mixing and/or grinding the compound with extenders, for example solvents, solid carriers and, optionally, surface-active compounds (surfactants).

The activity of the compositions according to the invention can be broadened considerably, and adapted to prevailing circumstances, by adding other insecticidally, acaricidally and/or fungicidally active ingredients. The mixtures of the compounds of formula (I) with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1-1 to 1-21 and Table 2 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+

TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin 1 (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin 1 (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, bipermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin 11 (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S(1037)+TX, demeton (1038)+TX, demeton-methyl (224)+TX, demeton-O (1038)+TX, demeton-O-methyl (224)+TX, demeton-S(1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name)

[CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin 1 (696)+TX, jasmolin 11 (696)+TX, jodfenphos (1248)+TX, juvenile hormone I (alternative name) [CCN]+TX, juvenile hormone II (alternative name) [CCN]+TX, juvenile hormone Ill (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin 1 (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+

TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiaben-dazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2](free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoximmethyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalo-nil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (dislosed in WO 2007/048556)+TX, 3-difluoromethyl-1-methyl-1H-pyrazole-4-carboxylic acid (3',4',5'-trifluoro-biphenyl-2-yl)-am ide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a, 12b-decahydro-6,12-dihydroxy-4,6a, 12b-trimethyl-11-oxo-9-(3-pyrid inyl)-2H, 11 Hnaphtho[2,1-b]pyrano[3,4-e]pyran-4-yl]methyl-cyclopropanecarboxylate [915972-17-7]+TX, 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxam ide [926914-55-8]+TX, flufiprole [704886-18-0]+TX, cyclaniliprole [1031756-98-5]+TX, tetraniliprole [1229654-66-3]+TX, guadipyr (described in WO2010/060231)+TX and cycloxaprid (described in WO 2005/077934)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright @ 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1-1 to 1-21 and Table 2 with active ingredients described above comprises a compound selected from Tables 1-1 to 1-21 and Table 2 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1-1 to 1-21 and Table 2 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1-1 to 1-21 and Table 2 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring —which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I.

The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring —which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

The following Examples illustrate, but do not limit, the invention.

The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm or 0.8 ppm.

PREPARATION EXAMPLES

The following non-limiting examples illustrate the above-described invention in greater detail without limiting it.

Example P1

Preparation of
5-chloro-2-hydroxy-4-methoxy-benzaldehyde

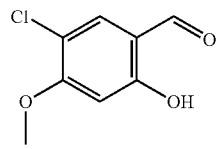

To a stirred solution of 2-hydroxy-4-methoxy-benzaldehyde (10 g, 65.725 mmol) in dichloromethane (50 ml) was added p-toluene sulfonic acid (5.65 g, 32.8625 mmol,) at room temperature. Resulting mixture was stirred at ambient temperature for 30 minutes. Reaction mixture was cooled to 0° C. and 1-chloropyrrolidine-2,5-dione (9.21 g., 69.0113 mmol) was added and then allowed to stir at ambient temperature for 5 h. Reaction mixture was diluted with dichloromethane (50 ml). Combined organic layer was washed with sodium bicarbonate solution (4×20 ml), and then with water (2×50 mL) followed by brine (50 mL). Organic layer was dried over $Na_2SO_4$, filtered and evaporated completely to afford the product 5-chloro-2-hydroxy-4-methoxy-benzaldehyde (12 g, 97.8482% of theoretical yield) as a gummy liquid.

$^1$H NMR (400 MHz, DMSO-d6) δ ppm 3.91 (s, 3 H) 6.68 (s, 1 H) 7.67 (s, 1 H) 10.03 (s, 1 H) 11.15 (s, 1 H)

Example P2

Preparation of (4-chloro-2-formyl-5-methoxy-phenyl) trifluoromethanesulfonate

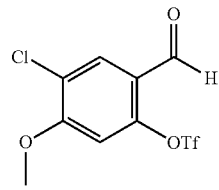 [SMILES: COc1cc(OS(=O)(=O)C(F)(F)F)c(C=O)cc1Cl]

To a stirred solution of 5-chloro-2-hydroxy-4-methoxy-benzaldehyde (12 g, 64.3107 mmol) and pyridine (14.13 g., 192.9323 mmol) in dichloromethane (50 ml) was added trifilic anhydride (20.4 g., 96.4661 mmol) at 0° C. Resulting mixture was stirred at ambient temperature for 3 hrs. Reaction mixture was diluted with dichloromethane (50 ml). Combined organic layer was washed with water (2×50 mL) followed by brine (50 mL), dried over Na$_2$SO$_4$, filtered and evaporated completely to afford the product (4-chloro-2-formyl-5-methoxy-phenyl) trifluoromethanesulfonate (17 g, 82.957% of theoretical yield) as a viscous brownish oil.

$^1$H NMR (400 MHz, CDCl$_3$) δ ppm 3.98-4.06 (m, 3 H) 5.74 (s, 1 H) 7.36 (s, 1 H) 8.19 (s, 1 H) 9.91 (s, J=7.83 Hz, 1 H)

Example P3

Preparation of 5-chloro-4-methoxy-2-(4,4,5,5-tetramethyl-1,3,2-dioxaborolan-2-yl)benzaldehyde

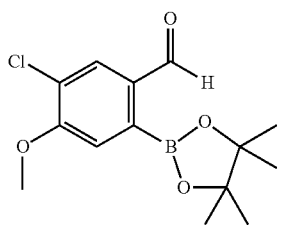 [SMILES: COc1cc(B2OC(C)(C)C(C)(C)O2)c(C=O)cc1Cl]

A mixture of (4-chloro-2-formyl-5-methoxy-phenyl) trifluoromethanesulfonate (5 g, 15.691 mmol), bis(pinacolato) diboron (7.56 g., 94.147 mmol,), KOAc (1.38 g., 47.074 mmol, and Pd(dppf)Cl$_2$.DCM complex (0.192 g., 0.78456 mmol,) in toluene (25 mL, 16V) was degassed for 5 minutes. The reaction mixture was then stirred at 95° C. for 2 hrs. TLC confirmed the completion of the reaction. The reaction mixture was poured in water (40 ml), aqueous layer was extracted with EtOAc (3×30 ml)

Combined organic layer was washed with water (2×250 mL) followed by brine (250 mL) and dried over Na$_2$SO$_4$, filtered and evaporated completely to give crude mass. The crude compound was purified by flash chromatography using 10% ethyl acetate in hexane as eluent to afford pure 5-chloro-4-methoxy-2-(4,4,5,5-tetramethyl-1,3,2-dioxaborolan-2-yl)benzaldehyde (3.6 g, 60% of theoretical yield) as white solid.

$^1$H NMR (400 MHz, DMSO-d6) δ ppm (s, 2 H) 1.20-1.28 (m, 15 H) 3.7 (m, 3 H) 7.11 (s, 1 H) 7.20 (s, 1 H) 7.83 (s, 1 H) 10.06 (s, 1 H)

Example P4

Preparation of 5-chloro-1-hydroxy-6-methoxy-3H-2,1-benzoxaborole

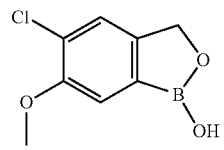

To a stirred solution of 5-chloro-4-methoxy-2-(4,4,5,5-tetramethyl-1,3,2-dioxaborolan-2-yl) benzaldehyde (5.5 g, 13 mmol) in methanol (25 mL), was added sodium borohydride in portions (0.6 g, 16 mmol) over a period of 15 mins at 0-5° C. Reaction mass was then stirred at ambient temperature. TLC confirmed the completion of the reaction. The reaction mixture was poured in water: Acetone mixture (40 ml) and methanol was evaporated off under vacuum. The aqueous layer was acidified with 6N HCl and stirred at ambient temperature overnight. The desired compound precipitated and the solid mass was filtered, washed with cyclohexane and dried under high vacuum to afford 5-chloro-1-hydroxy-6-methoxy-3H-2,1-benzoxaborole (2.9 g, 78% of theory) as a white solid.

$^1$H NMR (400 MHz, DMSO-d6) δ ppm 3.88 (s, 3 H) 4.92 (s, 2 H) 7.41 (s, 1 H) 7.51 (s, 1 H) 9.26 (s, 1 H)

LC-MS- M−H− 196.9 (RT; 1.56-1.59)

Example P5

Preparation of 5-chloro-1-hydroxy-3H-2,1-benzoxaborol-6-ol

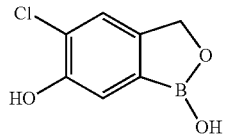

To a stirred solution of 5-chloro-1-hydroxy-6-methoxy-3H-2,1-benzoxaborole (1.6 g, 8.1 mmol) in dichloromethane (20 mL) at −78° C. was added BBr$_3$ (35 mL of 1M solution in dichloromethane) drop wise over 10 mins. Reaction mixture was stirred at RT for 2 hrs. When the TLC confirmed the completion of the reaction, reaction mass was quenched by drop wise addition of water.

The aqueous layer was extracted with EtOAc (3×30 ml). Combined organic layer was washed with water (2×250 mL), followed by brine (250 mL) and dried over Na$_2$SO$_4$, filtered and evaporated completely to afford the desired product 5-chloro-1-hydroxy-3H-2,1-benzoxaborol-6-ol (1.3 g, 87% of theoretical yield) as a white solid ¹H NMR (400 MHz, CDCl₃) δ ppm 4.86 (s, 2 H), 7.29 (s, 1 H) 7.39 (s, 1 H) 9.20 (br. s., 1 H) 10.10 (s, 1 H)

LC-MS- M+H- 185 (RT; 1.28-1.34)

Example P6

Preparation of 5-chloro-1-hydroxy-6-prop-2-ynoxy-3H-2,1-benzoxaborole

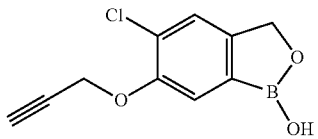

To a stirred solution of 5-chloro-1-hydroxy-3H-2,1-benzoxaborol-6-ol (0.1 g, 0.5 mmol) in DMF (2 ml), was added NaH (0.04 g., 2 mmol,) at 0-5° C. and stirred for 20 mins. 3-BROMO-1-PROPYNE (0.2 g 0.6 mmol) was added to the reaction mass and stirred at ambient temperature for 2 hrs. When the TLC confirmed the completion of the reaction, 1N HCl solution was added in drops till reaction mass turned acidic and aqueous layer was extracted with DCM (2×25 ml), which was evaporated off to get the crude product. The crude mass was purified by comb flash using 10-30% ethyl acetate in hexane to afford the desired product 5-chloro-1-hydroxy-6-prop-2-ynoxy-3H-2,1-benzoxaborole (0.08 g, 70% of theoretical yield) as a gummy solid 1H NMR (400 MHz, DMSO-d6) δ ppm 3.33 (s, 1 H)) 4.93 (s, 4 H) 7.50 (s, 1 H) 7.54 (s, 1 H) 9.31 (s, 1 H)

LC-MS- M-H- 221 (RT; 1.67-1.71)

Example P7

Preparation of 4-ethoxy-2-hydroxy-benzaldehyde

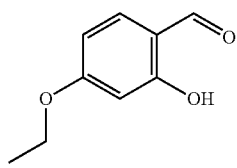

To a stirred solution of 2,4-dihydroxybenzaldehyde (1 g, 7.24 mmol) and K₂CO₃ (0.8og., 5.792 mmol,) in acetone (25 ml) was added bromoethane (1.78 g, 13.032 mmol,) in drops over a period of 10 minutes and refluxed overnight. When the TLC confirmed the completion of the reaction, reaction mass was acidified with 1N HCl. The aqueous layer was extracted with EtOAc (3×20 ml). Combined organic layer was washed with water (2×20 mL), followed by brine (20 mL) and dried over Na₂SO₄, filtered and evaporated completely to afford the desired product 4-ethoxy-2-hydroxy-benzaldehyde (1.1 g, 94% of theoretical yield)

1H NMR (400 MHz, DMSO-d6) δ ppm 1.41-1.49 (m, 3 H), 4.05-4.15 (m, 2 H), 6.40-6.43 (m, 1 H), 6.53 (dd, J=8.78, 2.26 Hz, H), 7.42 (d, J=8.53 Hz, 1 H), 9.71 (s, 1H) 11.49 (s, 1 H)

Example P8

Preparation of 5-chloro-4-ethoxy-2-hydroxy-benzaldehyde

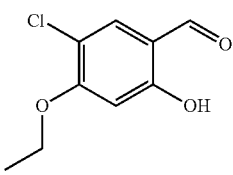

To a stirred solution of 4-ethoxy-2-hydroxy-benzaldehyde (1 g, 6.0177 mmol) in dichloromethane (20 ml) was added p-toluene sulfonic acid (0.51 g, 3.0089 mmol) at room temperature. Resulting mixture was stirred at ambient temperature for 30 minutes. Reaction mixture was cooled to 0° C. and 1-chloropyrrolidine-2,5-dione (0.82 g., 6.3186 mmol) was added and then allowed to stir at ambient temperature for 5 h. Reaction mixture was diluted with dichloromethane (20 ml). Combined organic layer was washed with sodium bicarbonate solution (4×10 ml), and then with water (2×20 mL) followed by brine (20 mL). Organic layer was dried over Na2SO4, filtered and evaporated completely to afford the product 5-chloro-4-ethoxy-2-hydroxy-benzaldehyde (0.82 g, 60% of theoretical yield) as a gummy liquid.

1H NMR (400 MHz, CDCl₃) δ ppm 1.41-1.46 (m, 3 H) 4.05-4.12 (m, 2 H) 6.40 (s, 1 H) 7.44 (s, 1 H) 9.61 (s, 1 H) 11.35 (s, 1 H)

Example P9

Preparation of (4-chloro-5-ethoxy-2-formyl-phenyl) trifluoromethanesulfonate

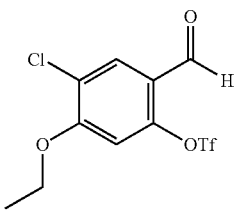 [SMILES: CCOc1cc(OS(=O)(=O)C(F)(F)F)c(C=O)cc1Cl]

To a stirred solution of 5-chloro-4-ethoxy-2-hydroxy-benzaldehyde (7.6 g, 38 mmol) and pyridine (9.1 g., 110 mmol) in dichloromethane (30 ml) was added triflic anhydride (13 g, 45 mmol) at 00° C. Resulting mixture was stirred at ambient temperature for 3 hrs. Reaction mixture was diluted with dichloromethane (50 ml). Combined organic layer was washed with water (2×50 mL) followed by brine (50 mL), dried over Na₂SO₄, filtered and evaporated completely to afford the product (4-chloro-5-ethoxy-2-formyl-phenyl) trifluoromethanesulfonate (11 g 87% of theoretical yield) as a viscous brownish oil.

1H NMR (400 MHz, CDCl₃) δ ppm 1.48 (t, J=7.03 Hz, 3 H) 4.15 (d, J=7.03 Hz, 2 H) 6.80 (s, 1 H) 7.93 (s, 1 H) 10.02 (s, 1 H)

Example P10

Preparation of 5-chloro-4-ethoxy-2-(4,4,5,5-tetramethyl-1,3,2-dioxaborolan-2-yl)benzaldehyde

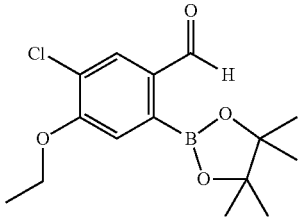 [SMILES: CCOc1cc(B2OC(C)(C)C(C)(C)O2)c(C=O)cc1Cl]

A mixture of (4-chloro-5-ethoxy-2-formyl-phenyl) trifluoromethanesulfonate (0.5 g, 2 mmol) in toluene (10 mL) was degassed for 5 minutes. Then were added bis(pinacolato)diboron (1 g, 5 mmol,), KOAc (0.4 g, 5 mmol, and Pd(dppf)Cl$_2$.DCM complex (0.06 g., 0.08 mmol,). The reaction mixture was then stirred at 95° C. for 2 hrs. TLC confirmed the completion of the reaction. The reaction mixture was poured in water (10 ml), aqueous layer was extracted with EtOAc (3×10 ml). Combined organic layer was washed with water (2×10 mL) followed by brine (10 mL) and dried over Na$_2$SO$_4$, filtered and evaporated completely to give crude mass. The crude compound was purified by flash chromatography using 10% ethyl acetate in hexane as eluent to afford pure 5-chloro-4-ethoxy-2-(4,4,5,5-tetramethyl-1,3,2-dioxaborolan-2-yl)benzaldehyde (0.4 g, 90% of theoretical yield) as white solid.

1H NMR (400 MHz, CDCl$_3$) δ ppm 1.36-1.45 (s, 12 H), 1.53 (t, J=7.03 Hz, 3 H), 4.26 (d, J=7.03 Hz, 2 H), 7.34 (s, 1 H) 8.03 (s, 1 H), 10.46 (s, 1 H)

Example P11

Preparation of 5-chloro-6-ethoxy-1-hydroxy-3H-2,1-benzoxaborole

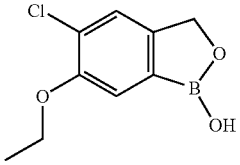

To a stirred solution of 5-chloro-4-ethoxy-2-(4,4,5,5-tetramethyl-1,3,2-dioxaborolan-2-yl)benzaldehyde (0.4 g, 1 mmol) in methanol (10 mL), was added sodium borohydride (0.06 g, 2 mmol) at 0-5 C. Reaction mass was then stirred at ambient temperature. TLC confirmed the completion of the reaction. The reaction mixture was poured in water: Acetone mixture (2 ml) and methanol was evaporated off under vacuum. The aqueous layer was acidified with 6N HCl and stirred at ambient temperature overnight. The desired compound precipitated and the solid mass was filtered, washed with cyclohexane and dried under high vacuum to afford 5-chloro-1-hydroxy-6-methoxy-3H-2,1-benzoxaborole (0.21 g, 80% of theory) as a white solid.

1H NMR (400 MHz, DMSO-d6) δ ppm 1.38 (t, J=6.90 Hz, 3 H) 4.12 (q, J=7.03 Hz, 2 H) 4.91 (s, 2 H) 7.39 (s, 1 H) 7.51 (s, 1 H) 9.24 (s, 1 H)

MS [M+H]+–: 211.1 (rt 6.2-6.3 min)

Example P12

Preparation of methyl 2-chloro-4-hydroxy-5-iodo-benzoate

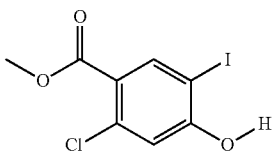

To a stirred solution of methyl 2-chloro-4-hydroxy-benzoate (12.5 g, 67.0 mmol) in ethanol (300 mL) were added at 0° C. iodine (17.0 g, 67.0 mmol) followed by silver sulfate (20.9 g, 67.0 mmol) by portions. The reaction mixture was stirred at 0-5° C. for 4 hrs. The reaction mixture was filtered. The cake was rinsed with ethyl acetate. The filtrate was washed twice with water. The organic layer was dried over sodium sulfate, filtered and concentrated under reduced pressure. The crude compound was purified by flash chromatography using 10% ethyl acetate in cyclohexane as eluent to afford pure methyl 2-chloro-4-hydroxy-5-iodo-benzoate (7.02 g, 33.5% of theoretical yield) as a white solid.

1H NMR (400 MHz, CDCl$_3$) δ ppm 3.90 (s, 3H) 5.69 (s, 1H) 7.08 (s, 1H) 8.26 (s, 1H)

Example P13

Preparation of methyl 2-chloro-4-hydroxy-5-methyl-benzoate

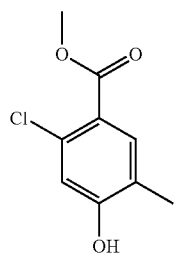

To a solution of methyl 2-chloro-4-hydroxy-5-iodo-benzoate (5.57 g, 17.8 mmol) in dioxane (54 mL) were added potassium carbonate (2.96 g, 21.4 mmol), trimethylboroxine (3.36 g, 3.74 ml, 26.7 mmol) and Pd(ddpf)Cl$_2$.DCM complex (0.522 g, 0.713 mmol). The mixture was irradiated in microwave 10 minutes at 150° C.

Then the mixture was cooled at room temperature, filtered over celite, the cake was rinsed with ethyl acetate. The filtrate was concentrated under reduced pressure. The crude was purified by flash chromatography using 10% ethyl acetate in cyclohexane as eluent to afford pure methyl 2-chloro-4-hydroxy-5-methyl-benzoate (2.264 g, 63.3% of theoretical yield) as a white solid.

1H NMR (400 MHz, CDCl$_3$) δ ppm 2.23 (s, 3H) 3.89 (s, 3H) 5.36 (s, 1H) 6.87 (s, 1H) 7.73 (s, 1H)

Example P14

Preparation of methyl 4-hydroxy-5-methyl-2-(4,4,5,5-tetramethyl-1,3,2-dioxaborolan-2-yl)benzoate

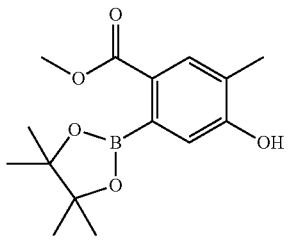 [SMILES: COC(=O)c1cc(C)c(O)cc1B1OC(C)(C)C(C)(C)O1]

A solution of methyl 2-chloro-4-hydroxy-5-methyl-benzoate (750 mg, 3.74 mmol) in dioxane (23 mL) was degassed for 5 minutes. Then were added tricyclohexylphosphine (168 mg, 0.598 mmol), bis(pinacolato)diboron (4.75 g, 18.7 mmol), potassium acetate (550 mg, 5.61 mmol) and Pd$_2$(dba)$_3$ (137 mg, 0.150 mmol). The mixture was irradiated in microwave for 40 minutes at 150° C. The mixture was filtered over celite. The filtrate was concentrated under reduced pressure. The crude was purified by flash chromatography using 15% ethyl acetate in cyclohexane as eluent to afford pure methyl 4-hydroxy-5-methyl-2-(4,4,5,5-tetramethyl-1,3,2-dioxaborolan-2-yl)benzoate (560 mg, 51.3% of theoretical yield) as a white solid.

$^1$H NMR (400 MHz, CDCl$_3$) δ ppm 1.41 (s, 12H) 2.23 (s, 3H) 3.87 (s, 3H) 5.22 (br. s., 1H) 6.82 (s, 1H) 7.75 (s, 1H)

Example P15

Preparation of methyl 4-ethoxy-5-methyl-2-(4,4,5,5-tetramethyl-1,3,2-dioxaborolan-2-yl)benzoate

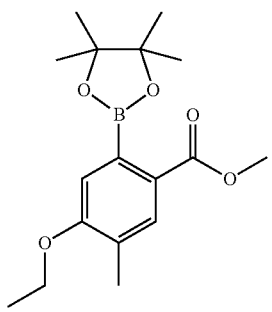 [SMILES: CCOc1cc(B2OC(C)(C)C(C)(C)O2)c(C(=O)OC)cc1C]

To a solution of methyl 4-hydroxy-5-methyl-2-(4,4,5,5-tetramethyl-1,3,2-dioxaborolan-2-yl)benzoate (440 mg, 1.056 mmol) in dimethylformamide (10 mL) was added at 0° C. potassium carbonate (333.1 mg, 2.410 mmol) then bromoethane (197 mg, 0.135 mL, 1.808 mmol). The mixture was stirred 10 minutes at 0° C. then 18 hrs at room temperature and then poured onto a mixture of ethyl acetate and water. The 2 layers were separated. The aqueous layer was extracted twice with ethyl acetate. The organic layers were combined, washed twice with water, once with brine, dried over sodium sulfate, filtered and concentrated under reduced pressure to afford methyl 4-ethoxy-5-methyl-2-(4,4,5,5-tetramethyl-1,3,2-dioxaborolan-2-yl)benzoate (458.2 mg, 95% of theoretical yield) as a beige solid.

$^1$H NMR (400 MHz, CDCl$_3$) δ ppm 1.43 (t, J=6.97 Hz, 3H) 1.45 (s, 12H), 2.21 (s, 3H), 3.87 (s, 3H), 4.10 (q, J=6.97 Hz, 2H), 6.82 (s, 1H), 7.74 (s, 1H)

Example P16

Preparation of 6-ethoxy-1-hydroxy-5-methyl-3H-2,1-benzoxaborole

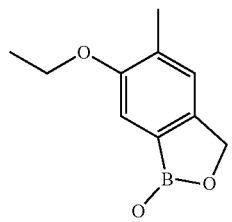

To a solution of methyl 4-ethoxy-5-methyl-2-(4,4,5,5-tetramethyl-1,3,2-dioxaborolan-2-yl)benzoate (233 mg, 0.7277 mmol) in ethanol (10 mL) was added by portions sodium borohydride (41.3 mg, 1.092 mmol) at 0° C. The reaction mixture was stirred 20 hrs at ambient temperature. Then water was added. Ethanol was evaporated under reduced pressure. HCl 6N (6 mL) was added. The reaction mixture was stirred 8 Hrs at ambient temperature.

The precipitated was filtered, rinsed with water and dried over reduced pressure to give a solid. Then, it was triturated in a mixture cyclohexane/Et$_2$O, filtered and dried under high vacuum to afford pure 6-ethoxy-1-hydroxy-5-methyl-3H-2,1-benzoxaborole (114.1 mg, 81.7% of theoretical yield) as a white solid (mp: 97-100° C.).

Example P17

Preparation of (4-chloro-2-formyl-6-methoxy-phenyl)trifluoromethanesulfonate

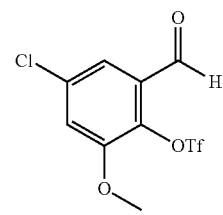 [SMILES: COc1cc(Cl)cc(C=O)c1OS(=O)(=O)C(F)(F)F]

To a stirred solution of 5-chloro-2-hydroxy-3-methoxy-benzaldehyde (2.5 g, 13 mmol) and pyridine (3.2 g., 40 mmol) in dichloromethane (25 ml) was added triflic anhydride (5.8 g, 20 mmol) at 00° C. Resulting mixture was stirred at ambient temperature for 3 hrs. Reaction mixture was diluted with dichloromethane (50 ml). Combined organic layer was washed with water (2×50 mL) followed by brine (50 mL), dried over Na2SO4, filtered and evaporated completely to afford the product (4-chloro-2-formyl-6-methoxy-phenyl) trifluoromethanesulfonate (1.6 g 37% of theoretical yield) as a viscous oil.

$^1$H NMR (400 MHz, DMSO-d6) δ ppm 10.20 (s, 1H), 7.51 (s, 1H), 7.27 (s, 2H), 3.98 (s, 3H)

Example P18

Preparation of 5-chloro-3-methoxy-2-(4,4,5,5-tetramethyl-1,3,2-dioxaborolan-2-yl)benzaldehyde

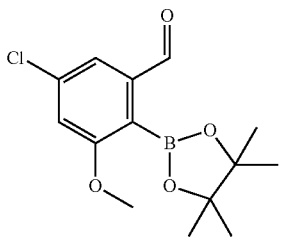 [SMILES: COc1cc(Cl)cc(C=O)c1B1OC(C)(C)C(C)(C)O1]

A solution of 4-chloro-2-formyl-6-methoxy-phenyl) trifluoromethanesulfonate (1.6 g, 5 mmol) in toluene (20 mL) was degassed for 5 minutes. Then were added bis(pinacolato)diboron (2 g, 7.5 mmol,), KOAc (1.5 g, 15 mmol, and Pd(dppf)Cl2.DCM complex (0.21 g., 0.25 mmol). The mixture was refluxed for 2 hrs at 110° C. The reaction mixture was diluted with water (10 ml), aqueous layer was extracted with EtOAc (3×10 ml). Combined organic layer was washed with water (2×10 mL) followed by brine (10 mL) and dried over Na2SO4, filtered and evaporated completely to give crude mass. The crude was purified by flash chromatography using 15% ethyl acetate in cyclohexane as eluent to afford pure methyl product 5-chloro-3-methoxy-2-(4,4,5,5-tetramethyl-1,3,2-dioxaborolan-2-yl)benzaldehyde (1.4 g, 94% of theoretical yield) as a white solid.

$^1$H NMR (400 MHz, DMSO-d6) δ ppm 9.88 (s, 1H), 7.39 (s, 1H), 7.06 (s, 1H), 3.83 (s, 3H), 1.45 (s, 12H)

Example P19

Preparation of 5-chloro-1-hydroxy-7-methoxy-3H-2,1-benzoxaborole

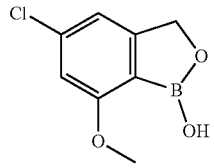

To a solution of methyl 5-chloro-3-methoxy-2-(4,4,5,5-tetramethyl-1,3,2-dioxaborolan-2-yl)benzaldehyde (400 mg, 0.1 mmol) in ethanol (4 mL) was added by portions sodium borohydride (100 mg, 3 mmol) at 0° C. The reaction mixture was stirred 20 hrs at ambient temperature. Then water was added. Ethanol was evaporated under reduced pressure. HCl 6N (6 mL) was added. The reaction mixture was stirred 8 Hrs at ambient temperature.

The precipitated was filtered, rinsed with water and dried over reduced pressure to give a solid. Then, it was triturated in a mixture cyclohexane/Et$_2$O, filtered and dried under high vacuum to afford pure 5-chloro-1-hydroxy-7-methoxy-3H-2,1-benzoxaborole (100 mg, 40% of theoretical yield) as a white solid (mp: ° C.).

MS [M–H]+: 197.4(rt 1.55-1.68 min)

$^1$H NMR (400 MHz, DMSO-d6) δ ppm 3.82 (s, 3 H) 4.91 (s, 2 H) 6.90 (s, 1 H) 7.06 (s, 1 H) 8.91 (s, 1 H)

Example 20

Preparation of 5,7-dichloro-1-hydroxy-3H-2,1-benzoxaborol-6-ol

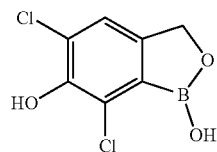

To a round bottom flask equipped with a stir bar, dichloromethane (50 mL, 100 mass %),5-chloro-1-hydroxy-3H-2,1-benzoxaborol-6-ol (0.50 g, 2.7 mmol, 100 mass %) and 4-methylbenzenesulfonic acid (0.23 g, 0.5 equiv., 1.4 mmol,) was added. The mixture was stirred for 20 mins at room temperature after which the chlorinating agent, 1-chloropyrrolidine-2,5-dione (0.38 g, 1.05 equiv., 2.8 mmol) was added portionwise at 0° C. Reaction mass was stirred for 4 hrs at room temperature. Reaction mixture was quenched with water, and organic layer was washed with water, dried over sodium sulphate and concentrated to get the desired product as a pale brown solid 5,7-dichloro-1-hydroxy-3H-2,1-benzoxaborol-6-ol (0.55 g, 2.5 mmol, 93% of theoretical yield)

MS [M–H]+: 216.7(rt 1.35 min)

$^1$H NMR (400 MHz, DMSO-d6) δ ppm 4.91 (s, 2 H) 7.45 (s, 1 H) 9.25 (s, 1 H) 9.90 (s 1 H)

Example 21

Preparation of 5,7-dichloro-6-ethoxy-1-hydroxy-3H-2,1-benzoxaborole

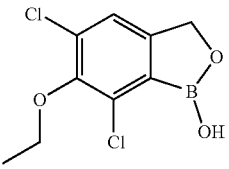

To a stirred solution of 5,7-dichloro-1-hydroxy-3H-2,1-benzoxaborol-6-ol (0.12 g, 0.55 mmol) in DMF (2 ml), NaH (0.07 g, 1.6 mmol) was added at 0-5° C. and stirred for 20 mins, after which bromoethane (0.15 g, 1.1 mmol) was added to the reaction mass and stirred the RM for 2 hrs at ambient temperature. The reaction mixture was then quenched with 1N HCl solution under cold condition, the solid precipitated out was filtered and washed with water. The crude solid thus obtained was purified by flash chromatography using 15% ethylacetate in cyclohexane as eluent to get the desired product as a white solid 5,7-dichloro-6-ethoxy-1-hydroxy-3H-2,1-benzoxaborole (0.055 g, 41% of theoretical yield)

$^1$H NMR (400 MHz, DMSO-d6) δ ppm 1.38 (t, J=7.03 Hz, 3H) 4.03 (q, J=7.11 Hz, 2 H) 4.94 (s, 2 H) 7.56 (s, 1 H) 9.29 (s, 1 H)

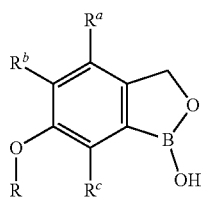

I-a

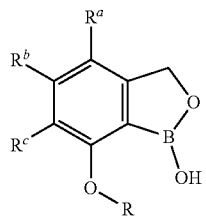

I-b

TABLE 2

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS [M − H]⁺ | RT |
|---|---|---|---|---|---|---|---|---|
| 1 | I-a | H | H | (CF₂-containing dioxolane group) | H | 147-149 | | |
| 2 | I-a | H | H | methyl | H | 119-121 | | |
| 3 | I-a | H | H | but-3-ynyl | H | 117-119 | | |
| 4 | I-a | H | H | methyl | Cl | 143-145 | | |
| 5 | I-a | H | Cl | methyl | H | — | | |
| 6 | I-a | H | Cl | H | H | 194-195 | | |
| 7 | I-a | H | Cl | but-3-ynyl | H | 129-131 | | |
| 8 | I-a | H | Cl | pent-3-ynyl | H | 165-166 | | |
| 9 | I-a | H | Cl | ethyl | H | 146-148 | | |
| 10 | I-a | H | Cl | 4-chlorobenzyl | H | 149-151 | | |
| 11 | I-a | H | Cl | —CO₂Me | H | 138-140 | | |
| 12 | I-a | H | Cl | acyl | H | 146-148 | | |
| 13 | I-a | H | H | H | Cl | 185-187 | | |
| 14 | I-a | H | NO₂ | methyl | H | 190-192 | | |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS [M − H]+ | RT |
|---|---|---|---|---|---|---|---|---|
| 15 | I-a | H | H | 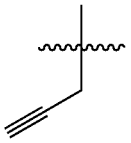 [SMILES: *CC#C] | Cl | — | 221 | 1.67-1.71 |
| 16 | I-a | H | NO$_2$ | H | H | 180-182 | | |
| 17 | I-a | H | Cl | CH$_2$CN | H | 211-213 | | |
| 18 | I-a | H | Cl | Tf | H | 113-115 | | |
| 19 | I-a | H | Cl | Ms | H | 142-144 | | |
| 20 | I-a | H | F | methyl | H | 182-184 | | |
| 21 | I-a | H | F | ethyl | H | 134-136 | | |
| 22 | I-a | H | H | methyl | F | 148-150 | | |
| 23 | I-a | H | Cl | 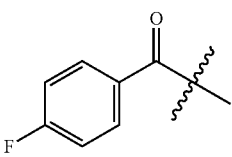 [SMILES: *C(=O)c1ccc(F)cc1] | H | 171-173 | | |
| 24 | I-a | H | Cl | 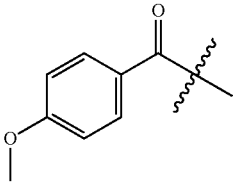 [SMILES: *C(=O)c1ccc(OC)cc1] | H | 141-143 | | |
| 25 | I-a | H | F | H | H | 152-154 | | |
| 26 | I-a | H | Cl | 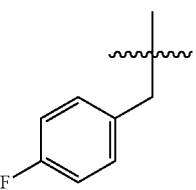 | H | 159-161 | | |
| 27 | I-a | H | Cl | 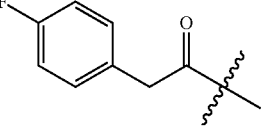 | H | 158-160 | | |
| 28 | I-a | H | F | 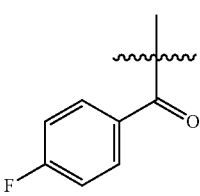 [SMILES: *C(=O)c1ccc(F)cc1] | H | 149-151 | | |
| 29 | I-a | H | Cl | 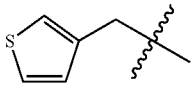 | H | 128-130 | | |

TABLE 2-continued
Table of selected examples and physical data
Tf means triflate (= trifluormethylsulfonyl), Ms means mesylate (methylsulfonyl),
n-Am means amyl (= n-pentyl) and n-Pr means n-propyl.
| CpdNo. (entry) | Formula | $R^a$ | $R^b$ | R | $R^c$ | m.p. (° C.) | MS $[M - H]^+$ | RT |
|---|---|---|---|---|---|---|---|---|
| 30 | I-a | H | F | 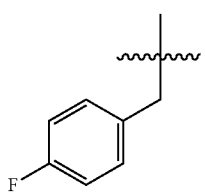 | H | 172-174 | | |
| 31 | I-a | H | F | 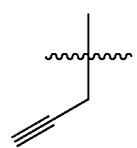 | H | 158-160 | | |
| 32 | I-a | H | F | 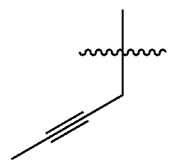 [SMILES: *CC#CC] | H | 154-155 | | |
| 33 | I-a | H | F | Ethanone | H | 127-129 | | |
| 34 | I-a | H | F | 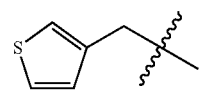 [SMILES: *Cc1ccsc1] | H | 148-150 | | |
| 35 | I-a | H | H | H | F | 175-177 | | |
| 36 | I-a | H | F | 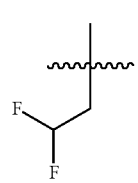 | H | 116-118 | | |
| 37 | I-a | H | H | ethyl | F | 106-108 | | |
| 38 | I-a | H | Me | ethyl | H | 97-100 | | |
| 39 | I-a | H | F | 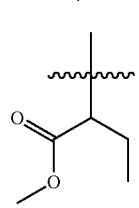 | H | — | 267.17 | 1.23 |
| 40 | I-a | H | F | 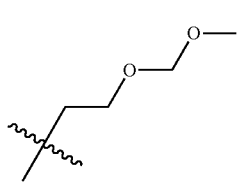 [SMILES: *CCOCOC] | H | — | 255.12 | 1.01 |
| 41 | I-a | H | F | 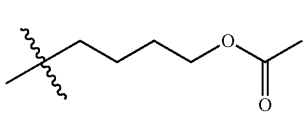 [SMILES: *CCCCOC(C)=O] | H | — | 281.18 | 1.24 |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS $[M-H]^+$ | RT |
|---|---|---|---|---|---|---|---|---|
| 42 | I-a | H | F | ethyl 4-pentanoate linker | H | — | 281.16 | 1.32 |
| 43 | I-a | H | F | methyl acetate linker | H | 136-137 | 239.09 | 0.93 |
| 44 | I-a | H | F | 2-methylene-3-cyanopropyl | H | — | 232.11 | 1.05 |
| 45 | I-a | H | F | tetrahydropyran-4-yl | H | — | 251.10 | 1.06 |
| 46 | I-a | H | F | dimethyl malonate linker | H | — | 297.17 | 1.00 |
| 47 | I-a | H | F | 2-hydroxypropyl linker | H | — | 225.04 | 0.66 |
| 48 | I-a | H | F | ethyl 2-methylpropanoate linker | H | — | 267.04 | 1.21 |
| 49 | I-a | H | F | 2-(2-methoxyethoxy)ethyl linker | H | — | 269.16 | 1.04 |

TABLE 2-continued
Table of selected examples and physical data
Tf means triflate (= trifluormethylsulfonyl), Ms means mesylate (methylsulfonyl),
n-Am means amyl (= n-pentyl) and n-Pr means n-propyl.
| CpdNo. (entry) | Formula | R$^a$ | R$^b$ | R | R$^c$ | m.p. (° C.) | MS [M − H]$^+$ | RT |
|---|---|---|---|---|---|---|---|---|
| 50 | I-a | H | F | 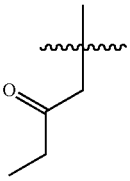 [SMILES: *CC(=O)CC] | H | — | 237.09 | 1.03 |
| 51 | I-a | H | F | 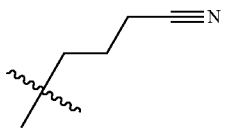 [SMILES: *CCCC#N] | H | — | 234.15 | 1.00 |
| 52 | I-a | H | F | 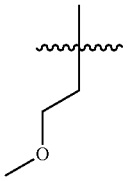 [SMILES: *CCOC] | H | — | 225.10 | 0.96 |
| 53 | I-a | H | F | 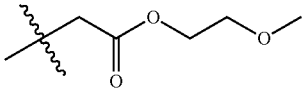 [SMILES: *CC(=O)OCCOC] | H | — | 283.14 | 0.98 |
| 54 | I-a | H | F | 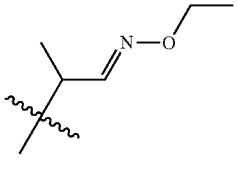 [SMILES: *C(C)/C=N/OCC] | H | — | 266.23 | 1.40 |
| 55 | I-a | H | F | 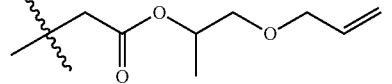 [SMILES: *CC(=O)OC(C)COCC=C] | H | — | 323.14 | 1.32 |
| 56 | I-a | H | F | 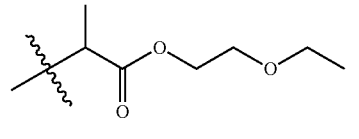 [SMILES: *C(C)C(=O)OCCOCC] | H | — | 311.15 | 1.26 |
| 57 | I-a | H | F | 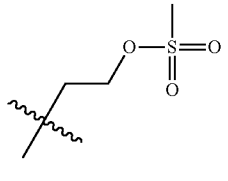 [SMILES: *CCOS(C)(=O)=O] | H | — | 289.09 | 0.93 |
| 58 | I-a | H | F | 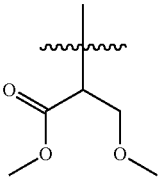 [SMILES: *C(COC)C(=O)OC] | H | — | 283.10 | 1.00 |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS [M − H]$^+$ | RT |
|---|---|---|---|---|---|---|---|---|
| 59 | I-a | H | F | (CH(CN)CH₃) | H | 127-129 | 220.04 | 1.05 |
| 60 | I-a | H | F | (CH₂CH=CHCO₂Et) | H | — | 279.19 | 1.30 |
| 61 | I-a | H | F | (CH₂CO₂Et) | H | — | 253.12 | 1.13 |
| 62 | I-a | H | F | (CH₂CO₂tBu) | H | — | 281.14 | 1.37 |
| 63 | I-a | H | F | (CH₂CH₂CH₂F) | H | — | 227.08 | 1.13 |
| 64 | I-a | H | F | (CH₂CH₂-1,3-dioxan-2-yl) | H | — | 281.15 | 1.13 |
| 65 | I-a | H | F | (CH₂CH₂CH₂Cl) | H | — | 243.01 | 1.33 |
| 66 | I-a | H | F | (CH₂CH₂Cl) | H | — | 229.08 | 1.23 |
| 67 | I-a | H | F | (CH₂CO₂iPr) | H | — | 267.10 | 1.44 |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS $[M - H]^+$ | RT |
|---|---|---|---|---|---|---|---|---|
| 68 | I-a | H | F | | H | — | 325.14 | 1.27 |
| 69 | I-a | H | F | | H | — | 253.21 | 1.22 |
| 70 | I-a | H | F | | H | — | 295.21 | 1.25 |
| 71 | I-a | H | F | | H | — | 276.21 | 1.07 |
| 72 | I-a | H | F | | H | — | 237.05 | 1.00 |
| 73 | I-a | H | F | | H | — | 281.54 | 0.62 |
| 74 | I-a | H | F | | H | — | 239.09 | 1.12 |
| 75 | I-a | H | F | | H | — | 213.03 | 0.97 |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | R$^a$ | R$^b$ | R | R$^c$ | m.p. (° C.) | MS [M − H]$^+$ | RT |
|---|---|---|---|---|---|---|---|---|
| 76 | I-a | H | Cl | | H | — | 229.22 | 1.15 |
| 77 | I-a | H | Cl | | H | — | 283.17 | 1.42 |
| 78 | I-a | H | Cl | | H | — | 271.08 | 1.20 |
| 79 | I-a | H | Cl | | H | — | 297.08 | 1.41 |
| 80 | I-a | H | Cl | | H | 155-157 | 255.10 | 1.11 |
| 81 | I-a | H | Cl | | H | — | 312.83 | 1.16 |
| 82 | I-a | H | Cl | | H | — | 250.07 | 1.19 |
| 83 | I-a | H | Cl | | H | — | 241.04 | 1.17 |
| 84 | I-a | H | Cl | | H | — | 339.16 | 1.47 |

TABLE 2-continued
Table of selected examples and physical data
Tf means triflate (= trifluormethylsulfonyl), Ms means mesylate (methylsulfonyl),
n-Am means amyl (= n-pentyl) and n-Pr means n-propyl.
| CpdNo. (entry) | Formula | R$^a$ | R$^b$ | R | R$^c$ | m.p. (° C.) | MS [M − H]$^+$ | RT |
|---|---|---|---|---|---|---|---|---|
| 85 | I-a | H | Cl | 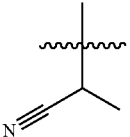 [SMILES: *C(C)C#N] | H | 138-140 | 235.99 | 1.24 |
| 86 | I-a | H | Cl | 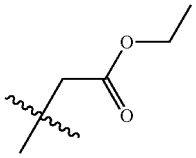 [SMILES: *CC(=O)OCC] | H | 128-130 | 269.08 | 1.25 |
| 87 | I-a | H | Cl | 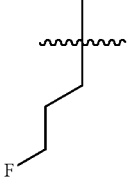 | H | — | 243.09 | 1.33 |
| 88 | I-a | H | Cl | 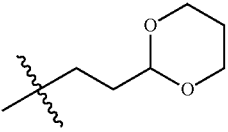 [SMILES: *CCC1OCCCO1] | H | — | 297.10 | 1.31 |
| 89 | I-a | H | Cl | 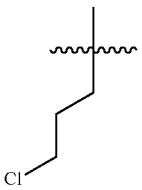 [SMILES: *CCCCl] | H | — | 259.07 | 1.48 |
| 90 | I-a | H | Cl | 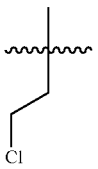 | H | — | 244.96 | 1.33 |
| 91 | I-a | H | Cl | 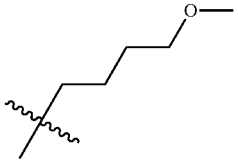 [SMILES: *CCCCOC] | H | — | 269.12 | 1.40 |
| 92 | I-a | H | Cl | 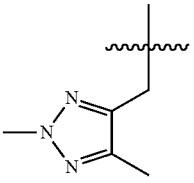 [SMILES: *Cc1nn(C)nc1C] | H | — | 292.10 | 1.25 |

TABLE 2-continued

Table of selected examples and physical data
Tf means triflate (= trifluormethylsulfonyl), Ms means mesylate (methylsulfonyl),
n-Am means amyl (= n-pentyl) and n-Pr means n-propyl.

| CpdNo. (entry) | Formula | $R^a$ | $R^b$ | R | $R^c$ | m.p. (° C.) | MS [M − H]⁺ | RT |
|---|---|---|---|---|---|---|---|---|
| 93 | I-a | H | Cl | –O–S(=O)(=O)–CH₂CH₂– (propyl sulfonate group) | H | — | 305.02 | 1.09 |
| 94 | I-a | H | Cl | H | Cl | 174-176 | | |
| 95 | I-a | H | Cl | ethyl | Cl | 109-111 | | |
| 96 | I-a | H | Cl | propargyl (CH₂–C≡CH) | Cl | 141-143 | | |
| 97 | I-a | H | Cl | H | Br | 151-153 | | |
| 98 | I-a | H | Cl | propargyl (CH₂–C≡CH) | Br | 162-164 | | |
| 99 | I-a | H | Cl | ethyl | Br | 133-135 | | |
| 100 | I-a | H | Cl | n-Am | H | 125-127 | | |
| 101 | I-a | H | Cl | n-Pr | H | 137-139 | | |
| 102 | I-a | H | H | methyl | Br | 130-132 | | |
| 103 | I-b | H | H | methyl | H | 83-85 | | |
| 104 | I-b | H | Cl | methyl | H | 146-148 | | |
| 105 | I-b | H | Cl | H | H | 159-161 | | |
| 106 | I-b | H | Cl | ethyl | H | 173-175 | | |
| 107 | I-b | H | H | methyl | Cl | 123-125 | | |

NMR Data for the compound 5 (1H-NMRdata:ppm (multiplicity/number of hydrogens)):

1HNMR(400 MHz, DMSO-d6) δ ppm 3.88(s, 1H) 4.92(s, 2H) 7.41(s, 2H) 7.51(s, 2H) 9.26(s, 1H)

The compound 1 (in the Table 2) has the following structure

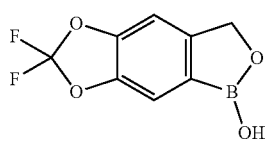 [SMILES: OB1OCc2cc3c(cc21)OC(F)(F)O3]

Characterising Data:

Table 2 shows selected melting point, The selected NMR data for compounds in the description were obtained as follows CDCl₃/D₂O and DMSO are used as solvents for NMR 400 MHz measurements. No attempt is made to list all characterising data in all cases.

In Table 2 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

m.p.=melting point b.p.=boiling point.
S=singlet br=broad
d=doublet dd=doublet of doublets
t=triplet q=quartet
m=multiplet ppm=parts per million The following LC-MS method was used to characterize the compounds:

ACQUITY SQD Mass Spectrometer from Waters (Single quadrupole mass spectrometer)

Ionisation method: Electrospray

Polarity: positive ions

Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700

Mass range: 100 to 800 Da

DAD Wavelength range (nm): 210 to 400

Method Waters ACQUITY UPLC with the Following HPLC Gradient Conditions (Solvent A: Water/Methanol 9:1,0.1% Formic Acid and Solvent B: Acetonitrile, 0.1% Formic Acid)

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

The characteristic values obtained for each compound were the retention time ("$R_t$", recorded in minutes) and the molecular ion as listed in Table 3.

Formulation examples for compounds of formula (I):

Example F-1.1 to F-1.2

Emulsifiable Concentrates

| Components | F-2.1 | F-2.2 |
| --- | --- | --- |
| A compound selected from the Tables 1-1 to 1-21 and Table 2 | 25% | 50% |
| calciumdodecylbenzenesulfonate | 5% | 6% |
| castoroilpolyethyleneglycolether (36 molethylenoxyunits) | 5% | — |
| tributylphenolpolyethyleneglycolether (30 molethylenoxyunits) | — | — |
| cyclohexanone | — | 20% |
| xylenemixture | 65% | 20% |

Emulsions of any desired concentration can be prepared by diluting such concentrates with water.

Example F-2

Emulsifiable Concentrate

| Components | F-2 |
| --- | --- |
| A compound selected from the Tables 1-1 to 1-21 and Table 2 | 10% |
| octylphenolpolyethyleneglycolether (4 to 5 mol ethylenoxy units) | 3% |
| Calcium dodecylbenzenesulfonate | 3% |
| Castoroilpolyglycolether (36 mol ethylenoxy units) | 4% |
| cyclohexanone | 30% |
| xylenemixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
| --- | --- | --- | --- | --- |
| A compound selected from the Tables 1-1 to 1-21 and Table 2 | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
| --- | --- | --- | --- | --- |
| A compound selected from the Tables 1-1 to 1-21 and Table 2 | 5% | 10% | 8% | 21% |
| Kaolin | 94% | — | 79% | 54% |
| highly dispersed silicic acid | 1% | — | 13% | 7% |
| Attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
| --- | --- | --- |
| A compound selected from the Tables 1-1 to 1-21 and Table 2 | 2% | 5% |
| highly dispersed silicic acid | 1% | 5% |
| Talcum | 97% | — |
| Kaolin | — | 90% |

Ready for use dusts are obtained by intimately mixing all components.

Examples F-6.1 to F-6.3

Wettable Powders

| Components | F-6.1 | F-6.2 | F-6.3 |
| --- | --- | --- | --- |
| A compound selected from the Tables 1-1 to 1-21 and Table 2 | 25% | 50% | 75% |
| sodium lignin sulfonate | 5% | 5% | — |
| sodium auryl sulphate | 3% | — | 5% |
| sodium diisobutylnaphthalene sulfonate | 6% | 10% | — |

-continued

| Components | F-6.1 | F-6.2 | F-6.3 |
|---|---|---|---|
| octylphenolpolyethylene glycol ether (7 to 8 mol ethylenoxy units) | 2% | — | — |
| highly dispersed silicic acid | 5% | 10% | 10% |
| Kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| Components | F-7 |
|---|---|
| A compound selected from the Tables 1-1 to 1-21 and Table 2 | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Biological Examples: Fungicidal Action

1. *Phytophthora infestans*/Tomato/Leaf Disc Preventative (Late Blight)

Tomato leaf disks were placed on water agar in multiwell plates (24-well format) and sprayed with the formulated test compound diluted in water at an application rate of 200 ppm. The leaf disks were inoculated with a spore suspension of the fungus 1 day after application. The inoculated leaf disks were incubated at 16° C. and 75% relative humidity under a light regime of 24 h darkness followed by 12/12 h (light/dark) in a climate cabinet and the activity of a compound was assessed as percent disease control compared to untreated when an appropriate level of disease damage appears in untreated check leaf disks (5-7 days after application). The compound 17, 82 and 85 (from Table 2) at 200 ppm give at least 80% disease control in this test when compared to untreated control leaf disks under the same conditions, which show extensive disease development.

2. *Plasmopara viticola*/Grape/Leaf Disc Preventative (Late Blight)

Grape vine leaf disks were placed on water agar in multiwell plates (24-well format) and sprayed with the formulated test compound diluted in water. The leaf disks were inoculated with a spore suspension of the fungus 1 day after application. The inoculated leaf disks were incubated at 19° C. and 80% relative humidity under a light regime of 12/12 h (light/dark) in a climate cabinet and the activity of a compound was assessed as percent disease control compared to untreated when an appropriate level of disease damage appears in untreated check leaf disks (6-8 days after application). The compounds 10, 15, 16, 17, 80, 85, 86, 87, 89, 90, 94, 95, 96 and 98 (from Table 2) at 200 ppm give at least 80% disease control in this test when compared to untreated control leaf disks under the same conditions, which show extensive disease development.

3. *Puccinia recondita* f. sp. *tritici*/Wheat/Leaf Disc Preventative (Brown Rust):

Wheat leaf segments cultivated variety (cv) Kanzler were placed on agar in 24-well plates and sprayed with formulated test compound diluted in water at an application rate of 200 ppm. The leaf disks were inoculated with a spore suspension of the fungus 1 day after application. The inoculated leaf segments were incubated at 19° C. and 75% relative humidity under a light regime of 12/12 h (light/dark) in a climate cabinet and the activity of a compound was assessed as percent disease control compared to untreated when an appropriate level of disease damage appears in untreated check leaf segments (7-9 days after application). The compounds 5, 7, 8, 10, 15, 26, 28, 32, 34, 44, 77, 80, 84, 86, 90, 95, 98, 99, 100 and 101 (from Table 2) at 200 ppm give at least 80% disease control in this test when compared to untreated control leaf disks under the same conditions, which show extensive disease development.

4. *Puccinia recondita* f. sp. *tritici*/Wheat/Leaf Disc Curative (Brown Rust)

Wheat leaf segments are placed on agar in multiwell plates (24-well format). The leaf disks are then inoculated with a spore suspension of the fungus. One day after inoculation the test solution is applied. After appropriate incubation the activity of a compound is assessed 8 dpi (days after inoculation) as curative fungicidal activity. Dose range: 200-22 ppm. The Compound 17, 39, 43, 80, 84 and 86 (from Table 2) at 200 ppm give at least 80% disease control in this test when compared to untreated control leaf disks under the same conditions, which show extensive disease development.

5. *Phaeosphaeria nodorum* (*Septoria nodorum*)/Wheat/Leaf Disc Preventative (Glume Blotch):

Wheat leaf segments cv Kanzler were placed on agar in a 24-well plate and sprayed with formulated test compound diluted in water at an application rate of 200 ppm. The leaf disks were inoculated with a spore suspension of the fungus 2 days after application. The inoculated test leaf disks were incubated at 20° C. and 75% relative humidity under a light regime of 12/12 h (light/dark) in a climate cabinet and the activity of a compound was assessed as percent disease control compared to untreated when an appropriate level of disease damage appears in untreated check leaf disks (5-7 days after application). The Compounds 7, 8, 15, 17, 32, 44, 100 and 106 (from Table 2) at 200 ppm give at least 80% disease control in this test when compared to untreated control leaf disks under the same conditions, which show extensive disease development.

6. *Magnaporthe grisea* (*Pyricularia oryzae*)/Rice/Leaf Disc Preventative (Rice Blast):

Rice leaf segments cv. *Ballila* were placed on agar in multiwell plate (24-well format) and sprayed with the formulated test compound diluted in water at an application rate of 200 ppm. The leaf segments were inoculated with a spore suspension of the fungus 2 days after application. The inoculated leaf segments were incubated at 22° C. and 80% rh under a light regime of 24 h darkness followed by 12/12 h (light/dark) in a climate cabinet and the activity of a compound was assessed as percent disease control compared to untreated when an appropriate level of disease damage appears in untreated check leaf segments (5-7 days after application). The Compound 7, 8, 32 and 104 (from Table 2) at 200 ppm give at least 80% disease control in this test when compared to untreated control leaf disks under the same conditions, which show extensive disease development.

7. *Pyrenophora teres*/Barley/Leaf Disc Preventative (Net Blotch):

Barley leaf segments cv. Hasso were placed on agar in a multiwell plate (24-well format) and sprayed with the formulated test compound diluted in water. The leaf segments were inoculated with a spore suspension of the fungus 2 days after application. The inoculated leaf segments were incubated at 20° C. and 65% rh under a light regime of 12 h light/12 h darkness in a climate cabinet and the activity of a compound was assessed as disease control compared to untreated when an appropriate level of disease damage appears in untreated check leaf segments (5-7 days after application). The Compound 8 and 76 (from Table 2) at 200 ppm give at least 80% disease control in this test when compared to untreated control leaf disks under the same conditions, which show extensive disease development.

8. *Alternaria solani*/Tomato/Leaf Disc (Early Blight)

Tomato leaf disks cultivated variety (cv.) Baby were placed on agar in multiwell plates (24-well format) and sprayed with the formulated test compound diluted in water at an application rate of 200 ppm. The leaf disks were inoculated with a spore suspension of the fungus 2 days after application. The inoculated leaf disks were incubated at 23° C./21° C. (day/night) and 80% relative humidity under a light regime of 12/12 h (light/dark) in a climate cabinet and the activity of a compound was assessed as percent disease control compared to untreated when an appropriate level of disease damage appears on untreated check disk leaf disks (5-7 days after application). The Compounds (from table T1 and Tx) 31, 76, 104 and 106 at 200 ppm give at least 80% disease control in this test when compared to untreated control leaf disks under the same conditions, which show extensive disease development.

9. *Pythium ultimum*/Liquid Culture (Seedling Damping Off)

Mycelia fragments and oospores of a newly grown liquid culture of the fungus were directly mixed into nutrient broth (potato dextrose broth). After placing a DMSO solution of test compound into a 96-well format microtiter plate at an application rate of 20 ppm, the nutrient broth containing the fungal mycelia/spore mixture was added. The test plates were incubated at 24° C. and the inhibition of growth was determined photometrically 2-3 days after application. The Compounds 1, 2, 3, 4, 5, 6, 7, 8, 9, 10, 11, 12, 13, 14, 15, 16, 17, 18, 19, 20, 21,22,23,24,25,27, 28, 31,32,33,34,35, 36,37, 38, 39, 40, 41,42, 43, 44, 45, 46, 48, 49, 50, 51,52, 53, 54, 55, 56, 57, 58, 59, 60, 61,63, 64, 65, 66, 67, 68, 69, 70, 71,72, 73, 74, 75, 76, 77, 78, 79, 80, 81, 82, 83, 84, 85, 86, 87, 88, 89, 90, 92, 93, 94, 95, 96, 97, 98, 99, 101, 103, 104, 105, 106 and 107 (from Table 2) at 20 ppm give at least 80% disease control in this test when compared to untreated control leaf disks under the same conditions, which show extensive disease development.

10. *Botryotinia fuckeliana* (*Botrytis cinerea*)/Liquid Culture (Gray Mould):

Conidia of the fungus from cryogenic storage were directly mixed into nutrient broth (Vogels broth). After placing a DMSO solution of test compound into a 96-well microtiter plate at an application rate of 20 ppm, the nutrient broth containing the fungal spores was added. The test plates were incubated at 24° C. and the inhibition of growth was determined photometrically 3-4 days after application. The Compounds 1, 2, 3, 4, 7, 8, 9, 12, 20, 21 and 103 (from Table 2) at 20 ppm give at least 80% disease control in this test when compared to untreated control leaf disks under the same conditions, which show extensive disease development.

11. *Glomerella lagenarium* (*Colletotrichum lagenarium*)/Liquid Culture (Anthracnose):

Conidia of the fungus from cryogenic storage were directly mixed into nutrient broth (PDB potato dextrose broth). After placing a DMSO solution of test compound into a 96-well microtiter plate at an application rate of 20 ppm, the nutrient broth containing the fungal spores was added. The test plates were incubated at 24° C. and the inhibition of growth was measured photometrically 3-4 days after application. The Compounds 1,3, 4, 5, 6, 7, 8, 9, 12, 15, 16, 17, 18, 20, 21,23, 24, 28, 29, 31,32, 33, 37, 38, 39, 43, 44, 50, 54, 59, 60, 66, 74, 76, 80, 83, 85, 86, 87, 89, 90, 95, 99, 100, 101, 103, 104, 105, 106 and 107 (from Table 2) at 20 ppm give at least 80% disease control in this test when compared to untreated control leaf disks under the same conditions, which show extensive disease development.

12. *Mycosphaerella arachidis* (*Cercospora arachidicola*)/Liquid Culture (Early Leaf Spot):

Conidia of the fungus from cryogenic storage were directly mixed into nutrient broth (PDB potato dextrose broth). After placing a DMSO solution of test compound into a 96-well microtiter plate at an application rate of 20 ppm, the nutrient broth containing the fungal spores was added. The test plates were incubated at 24° C. and the inhibition of growth was determined photometrically 4-5 days after application. The Compounds 1,2, 3, 4, 5, 6, 7, 8, 9, 11, 12, 13, 15, 16, 17, 18, 20, 21,22, 27, 31, 32, 35, 37, 38, 39, 44, 49, 50, 59, 66, 74, 75, 76, 77, 80, 83, 85, 86, 87, 90, 94, 95, 96, 97, 99, 101, 103, 104, 105, 106 and 107 (from Table 2) at 20 ppm give at least 80% disease control in this test when compared to untreated control leaf disks under the same conditions, which show extensive disease development.

13. *Mycosphaerella graminicola* (*Septoria tritici*)/Liquid Culture (*Septoria* Blotch):

Conidia of the fungus from cryogenic storage were directly mixed into nutrient broth (PDB potato dextrose broth). After placing a DMSO solution of test compound into a 96-well microtiter plate at an application rate of 20 ppm, the nutrient broth containing the fungal spores was added. The test plates were incubated at 24° C. and the inhibition of growth was determined photometrically 4-5 days after application. The Compounds 1, 3, 4, 5, 6, 7, 8, 9, 10, 11, 12, 13, 15, 16, 17, 18, 21, 22, 28, 29, 31, 32, 33, 34, 37, 38, 44, 89, 90, 94, 95, 96, 97, 98, 99, 100, 101, 103, 104, 105 and 107 (from Table 2) at 20 ppm give at least 80% disease control in this test when compared to untreated control leaf disks under the same conditions, which show extensive disease development.

14. *Gaeumannomyces graminis*/Liquid Culture (Take-all of Cereals):

Mycelial fragments of the fungus from cryogenic storage were directly mixed into nutrient broth (PDB potato dextrose broth). After placing a DMSO solution of test compound into a 96-well microtiter plate at an application rate of 20 ppm, the nutrient broth Cp.33, containing the fungal spores is added. The test plates were incubated at 24° C. and the inhibition of growth was determined photometrically 4-5 days after application. The Compounds 1, 2, 3, 4, 5, 6, 7, 8, 9, 10, 11, 12, 13, 15, 20, 21, 31, 32, 33, 36, 37, 38, 43, 44, 50, 54, 59, 60, 63, 66, 74, 75, 76, 77, 80, 81, 83, 85, 86, 87, 89, 90, 94, 95, 96, 97, 98, 99, 100, 101 and 103 (from Table 2) at 20 ppm give at least 80% disease control in this test when compared to untreated control leaf disks under the same conditions, which show extensive disease development.

15. *Monographella nivalis* (*Microdochium nivale*)/Liquid Culture (Foot Rot Cereals):

Conidia of the fungus from cryogenic storage were directly mixed into nutrient broth (PDB potato dextrose broth). After placing a DMSO solution of test compound into a 96-well microtiter plate at an application rate of 20 ppm, the nutrient broth containing the fungal spores was added. The test plates were incubated at 24° C. and the inhibition of growth was determined photometrically 4-5 days after application. The Compounds 1,2, 3, 4, 5, 6, 7, 8, 9, 10, 11, 12, 13, 14, 15, 16, 17, 18, 19, 20, 21, 22, 23, 24, 25, 26, 27, 28, 29, 31, 32, 33, 34, 35, 36, 37, 38, 43, 44, 50, 52, 59, 60, 63, 65, 66, 74, 76, 77, 80, 83, 85, 86, 87, 88, 89, 90, 94, 95, 96, 97, 99, 100, 101, 103, 104, 105, 106 and 107 (from Table 2) at 20 ppm give at least 80% disease control in this test when compared to untreated control leaf disks under the same conditions, which show extensive disease development.

16. *Fusarium culmorum*/Liquid Culture (Head Blight):

Conidia of the fungus from cryogenic storage were directly mixed into nutrient broth (PDB potato dextrose broth). After placing a (DMSO) solution of the test compounds into a microtiter plate (96-well format), the nutrient broth containing the fungal spores was added. The test plates were incubated at 24° C. and the inhibition of growth was determined visually 3-4 days after application. The Compounds 1, 3, 4, 7, 8, 9, 12, 17, 20, 21,22, 28, 31,32, 33, 37, 38, 39, 43, 48, 50, 59, 74, 80, 85, 86, 96, 101, 103, 104, 105, 106 and 107 (from Table 2) at 20 ppm give at least 80% disease control in this test when compared to untreated control leaf disks under the same conditions, which show extensive disease development.

17. *Thanatephorus cucumeris* (*Rhizoctonia solani*)/Liquid Culture (Foot Rot, Damping-Off):

Mycelia fragments of a newly grown liquid culture of the fungus were directly mixed into nutrient broth (PDB potato dextrose broth). After placing a DMSO solution of the test compounds into a 96-well microtiter plate at an application rate of 20 ppm, the nutrient broth containing the fungal material was added. The test plates were incubated at 24° C. and the inhibition of growth was determined photometrically 3-4 days after application. The Compounds 1, 3, 7, 8, 9, 11, 13, 14, 15, 16, 17, 18, 22, 31, 32, 37, 43, 44, 50, 60, 61, 80, 84, 86, 94, 95, 96, 99, 101, 104, 106 and 107 (from Table 2) at 20 ppm give at least 80% disease control in this test when compared to untreated control leaf disks under the same conditions, which show extensive disease development.

18. *Sclerotinia sclerotiorum*/Liquid Culture (Cottony Rot):

Mycelia fragments of a newly grown liquid culture of the fungus were directly mixed into nutrient broth (PDB potato dextrose broth). After placing a (DMSO) solution of the test compounds into a microtiter plate (96-well format) the nutrient broth containing the fungal material was added. The test plates were incubated at 24° C. and the inhibition of growth was determined visually 3-4 days after application. The Compounds 1, 2,3,4,5,7, 8, 9, 11, 13, 15, 17, 20, 21,22,31,32,33,36,37, 38, 43,44,48, 50, 52, 59, 74, 75, 76, 77, 80, 85, 86, 95, 96, 99, 101, 103, 104, 105, 106 and 107 (from Table 2) at 20 ppm give at least 80% disease control in this test when compared to untreated control leaf disks under the same conditions, which show extensive disease development.

The invention claimed is:
1. A compound of Formula I-a

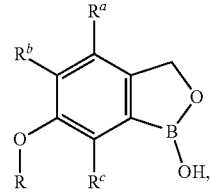

wherein
$R^a$ is H;
$R^b$ is fluorine, chlorine, methyl or ethyl; and
$R^c$ is H, fluorine, chlorine, bromine; and
R is H, $C_{1-5}$-alkyl, $C_{1-5}$-alkylacyl, acetyl, formyl,

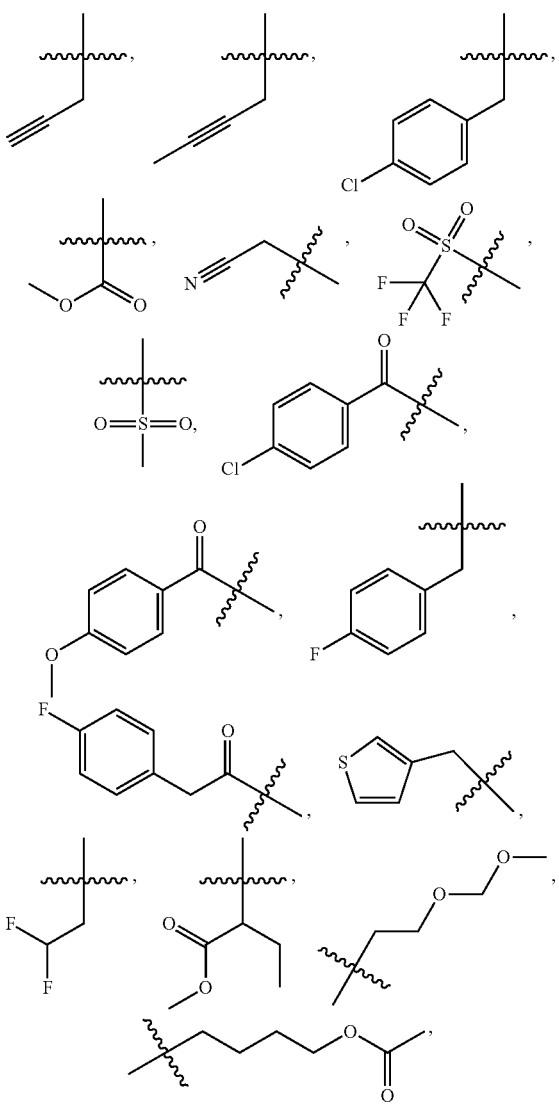

-continued

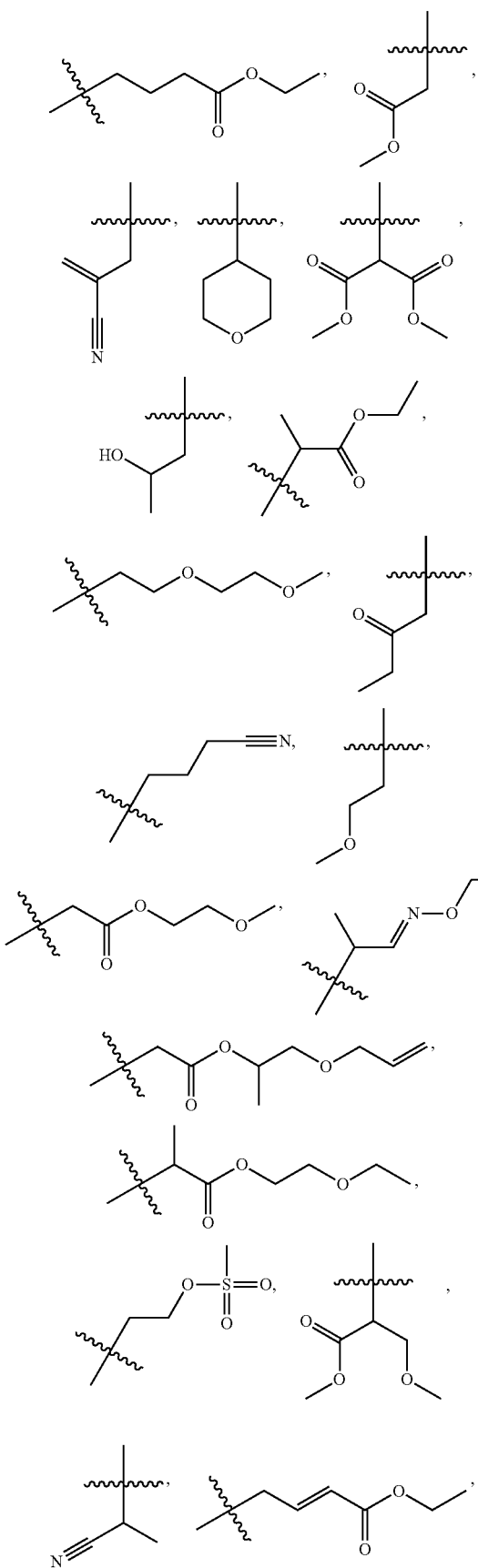

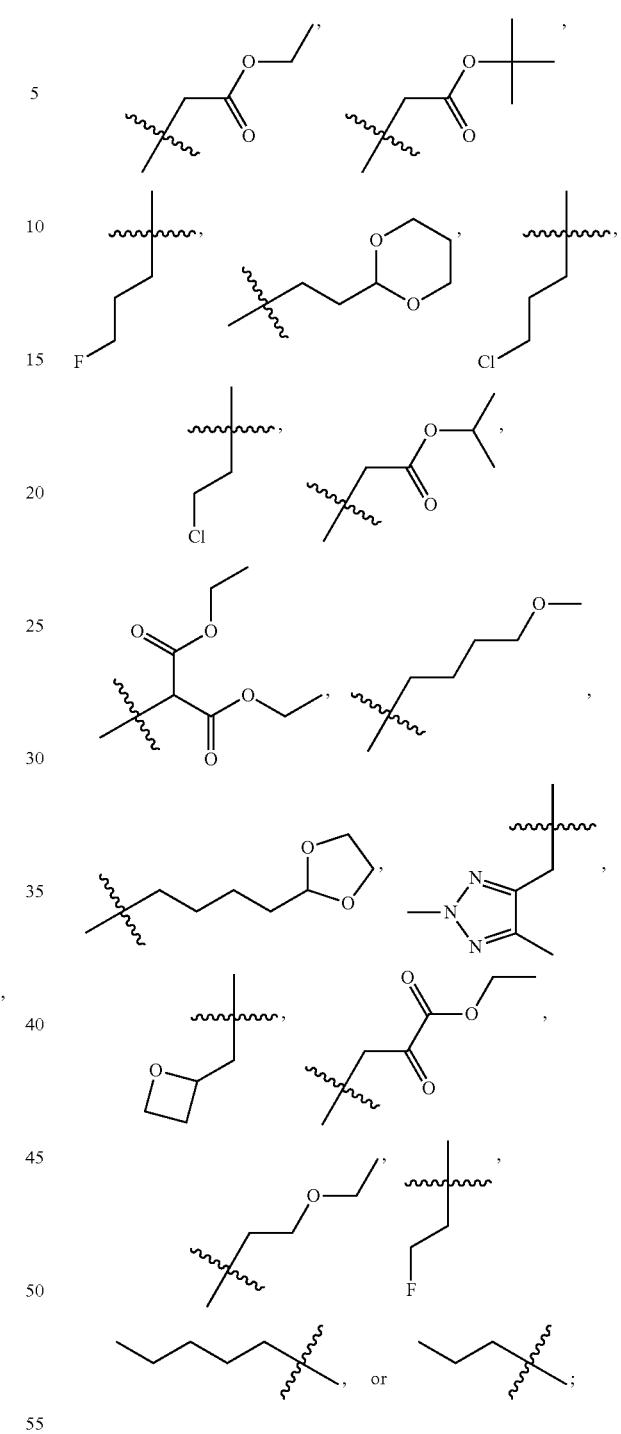

or an agronomically acceptable salt, stereoisomer, diastereoisomer, enantiomer, tautomer, atriopisomer or N-oxide thereof.

2. A composition for controlling and protecting against phytopathogenic microorganisms, comprising a compound of formula I-a as defined in claim 1 and at least one auxiliary.

3. A composition comprising a fungicidally effective amount of a compound of formula I-a as defined in claim 1, optionally comprising at least one additional active ingredient.

4. A compound of formula (I)

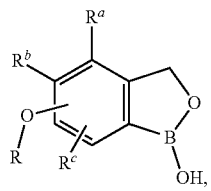

wherein
$R^a$ is H;
$R^b$ is fluorine, chlorine;
$R^c$=H, fluorine, chlorine, $C_1$-$C_2$alkoxy or $C_1$-$C_2$ haloalkoxy; and
R is ethyl, methyl, propargyl, C(O)R'; wherein R' is $C_2$-$C_6$alkyl; and wherein R does not form a ring with either $R^b$ or $R^c$;
or an agronomically acceptable salt, stereoisomer, diastereoisomer, enantiomer, tautomer, atriopisomer or N-oxide thereof.

5. A compound of formula (I) according to claim 4, wherein
$R^a$ is H;
$R^b$ is chlorine or fluorine;
$R^c$=H, fluorine or chlorine; and
R is ethyl, methyl or propargyl.

6. A compound of formula (I) according to claim 4, wherein the compound of formula (I) has the formula I-b

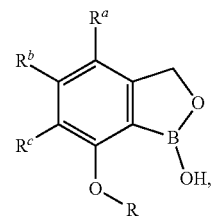

wherein
$R^a$ is H;
$R^b$ is fluorine, chlorine;
$R^c$=H, fluorine, chlorine; and
R is H, $C_2$-$C_6$alkyl.

7. A method of controlling or preventing infestation of useful plants by phytopathogenic microorganisms, wherein a compound of formula I-a as defined in claim 1 as active ingredient, is applied to the plants, to parts thereof or the locus thereof.

8. A method of controlling phytopathogenic diseases on useful plants or plant propagation material thereof, which comprises applying to said plant propagation material a fungicidally effective amount of a plant propagation material protecting composition comprising a compound of formula I-a as defined in claim 1 together with a suitable carrier therefor.

* * * * *